US009265746B2

(12) United States Patent
Moser et al.

(10) Patent No.: US 9,265,746 B2
(45) Date of Patent: Feb. 23, 2016

(54) METHOD FOR CELL-SPECIFIC TARGETING

(75) Inventors: Rudolf Moser, Schaffhausen (CH); Viola Groehn, Dachsen (CH); Roger Schibli, Baden (CH); Cristina Magdalena Mueller, Rotterdam (CH)

(73) Assignee: MERCK & CIE, Schaffhausen (CH)

( * ) Notice: Subject to any disclaimer, the term of this patent is extended or adjusted under 35 U.S.C. 154(b) by 1529 days.

(21) Appl. No.: 11/443,442

(22) Filed: May 31, 2006

(65) Prior Publication Data

US 2007/0280880 A1     Dec. 6, 2007

(51) Int. Cl.
*A61K 31/22*    (2006.01)
*A61K 31/525*   (2006.01)
*A61K 51/04*    (2006.01)
*A61K 48/00*    (2006.01)

(52) U.S. Cl.
CPC .............. *A61K 31/22* (2013.01); *A61K 31/525* (2013.01); *A61K 51/0459* (2013.01); *A61K 48/00* (2013.01)

(58) Field of Classification Search
CPC ...................................................... A61K 31/22
See application file for complete search history.

(56) References Cited

U.S. PATENT DOCUMENTS 3,856,959 A * 12/1974 Mead ............................ 514/249
5,030,634 A *  7/1991 Krumdieck et al. .......... 514/249

FOREIGN PATENT DOCUMENTS

WO    WO 2004082463 A2 *  9/2004

OTHER PUBLICATIONS

Siegel et al 'Evaluation of 111In-DTPA-Folate as a Receptor-Targeted Diagnostic Agent for Ovarian Cancer: Initial Clinical Results' The Journal of Nuclear Medecine, 44(5), p. 700-707, 2003.*
Nonancourt-Didion et al Overexpression of folate binding protein alpha is one of the mechanism explaining the adaptation of HT29 to high concentratoin of methrotrexate Cancer Letters, vol. 171, p. 139-145, 2001.*
Imam, Seyed K. 'Status of Radioimmunotherapy in the New Millenium' Cancer Biotherapy and Radiopharmaceuticals, 16(3), p. 237-256, 2001.*
Kassis Al. The amazing world of auger electrons. Int J Radiat Biol. Nov.-Dec. 2004;80(11-12):789-803.*
Ke CY, Mathias CJ, Green MA. The folate receptor as a molecular target for tumor-selective radionuclide delivery. Nucl Med Biol. Nov. 2003;30(8):811-7.*
Long HJ, Langdon RM Jr, Cha SS, Veeder MH, Pfeifle DM, Krook JE, Ebbert LP, Tschetter LK, Roshon SG. Phase II trial of methotrexate, vinblastine, doxorubicin, and cisplatin in advanced/recurrent endometrial carcinoma. Gynecol Oncol. Aug. 1995;58(2):240-3.*

Elnakat H, Ratnam M. Distribution, functionality and gene regulation of folate receptor isoforms: implications in targeted therapy. Adv. Drug Deliv. Rev. 2004; 56:1067-84.
Paulos CM, Turk MJ, Breur GJ, Low PS. Folate receptor-mediated targeting of therapeutic and imaging agents to activated macrophages in rheumatoid arthritis. Adv. Drug Deliv. Rev. 2004; 56:1205-17.
Leamon CP, Low PS. Folate-mediated targeting: from diagnostics to drug and gene delivery. Drug Discov. Today 2001; 6:44-51.
Leamon CP, Reddy JA. Folate-targeted chemotherapy. Adv. Drug Deliv. Rev. 2004; 56:1127-41.
Leamon CP, Reddy JA, Vlahov IR, et al. Synthesis and biological evaluation of EC72: a new folate-targeted chemotherapeutic. Bioconjugate Chem. 2005; 16:803-11.
Ward CM, Acheson N, Seymour LW. Folic acid targeting of protein conjugates into ascites tumour cells from ovarian cancer patients. J. Drug Target. 2000; 8:119-23.
Leamon CP, Pastan I, Low PS. Cytotoxicity of folate-pseudomonas exotoxin conjugates toward tumor cells—contribution of translocation domain. J. Biol. Chem. 1993; 268:24847-54.
Leamon CP, Low PS. Selective targeting of malignant cells with cytotoxin-folate conjugates. J. Drug Target. 1994; 2:101-12.
Li S, Deshmukh HM, Huang L. Folate-mediated targeting of antisense oligodeoxynucleotides to ovarian cancer cells. Pharm. Res. 1998; 15:1540-45.
Zhao XBB, Lee RJ. Tumor-selective targeted delivery of genes and antisense oligodeoxyribonucleotides via the folate receptor. Adv. Drug Deliv. Rev. 2004; 56:1193-204.
Lee RJ, Low PS. Folate-mediated tumor cell targeting of liposome-entrapped doxorubicin in vitro. Biochim. Biophys. Acta-Biomembr. 1995; 1233:134-44.
Gabizon A, Shmeeda H, Horowitz AT, Zalipsky S. Tumor cell targeting of liposome-entrapped drugs with phospholipid-anchored folic acid-PEG conjugates. Adv. Drug Deliv. Rev. 2004; 56:1177-92.
Konda SD, Aref M, Wang S, Brechbiel M, Wiener EC. Specific targeting of folate-dendrimer MRI contrast agents to the high affinity folate receptor expressed in ovarian tumor xenografts. Magn. Reson. Mat. Phys. Biol. Med. 2001; 12:104-13.
Mathias CJ, Wang S, Waters DJ, et al. Indium-111-DTPA-folate as a potential folate-receptor-targeted radiopharmaceutical. J. Nucl. Med. 1998; 39:1579-85.
Mathias CJ, Green MA. A kit formulation for preparation of [111In]In-DTPA-folate, a folate-receptor-targeted radiopharmaceutical. Nucl. Med. Biol. 1998; 25:585-87.
Mathias CJ, Green MA. Alternative kit formulations for compounding of 111 In-DTPA-folate (folatescan). J. Nucl. Med. 2000; 41:1113.
Siegel BA, Dehdashti F, Mutch DG, et al. Evaluation of 111In-DTPA-folate as a receptor-targeted diagnostic agent for ovarian cancer: initial clinical results. J. Nucl. Med. 2003; 44:700-07.
Leamon CP, Parker MA, Vlahov IR, et al. Synthesis and biological evaluation of EC20: a new folate- derived, 99mTc-based radiopharmaceutical. Bioconjugate Chem. 2002; 13:1200-10.
Reddy JA, Xu LC, Parker N, Vetzel M, Leamon CP. Preclinical evaluation of 99mTc-EC20 for imaging folate receptor-positive tumors. J. Nucl. Med. 2004; 45:857-66.

(Continued)

*Primary Examiner* — Paul Zarek
(74) *Attorney, Agent, or Firm* — Millen, White, Zelano, Branigan, P.C.

(57) ABSTRACT

Method for selective targeting of one or more effector moiety such as diagnostic or a therapeutic agent to a cell or population of cells expressing a folate-receptor comprising simultaneous or sequential administration of an antifolate with a folate- or pteroate-conjugate comprising said one or more effector moiety.

33 Claims, 6 Drawing Sheets

(56) References Cited

OTHER PUBLICATIONS

Mathias CJ, Hubers D, Low PS, Green MA. Synthesis of [99mTc]DTPA-folate and its evaluation as a folate-receptor-targeted radiopharmaceutical. Bioconjugate Chem. 2000; 11:253-57.

Trump DP, Mathias CJ, Yang ZF, et al. Synthesis and evaluation of 99mTc(CO)3-DTPA-folate as a folate-receptor-targeted radiopharmaceutical. Nucl. Med. Biol. 2002; 29:569-73.

Wang S, Luo J, Lantrip DA, et al. Design and synthesis of [111In]DTPA-folate for use as a tumor-targeted radiopharmaceutical. Bioconjugate Chem. 1997; 8:673-79.

Müller C, Dumas C, Hoffmann U, Schubiger PA, Schibli R. Organometallic 99mTc-technetium(I)- and Re-rhenium(I)-folate derivatives for potential use in nuclear medicine. J. Organomet. Chem. 2004; 689:4712-21.

Alberto R, Schibli R, Egli A, et al. Metal carbonyl syntheses. XXII. Low-pressure carbonylation of [MOCl4]- and [MO4]-. The technetium(I) and rhenium(I) complexes [NEt4]2[MCl3(CO)3]. J. Organomet. Chem. 1995; 492:217-24.

Alberto R, Ortner K, Wheatley N, Schibli R, Schubiger AP. Synthesis and properties of boranocarbonate: a convenient in situ CO source for the aqueous preparation of [99mTc(OH2)3(CO)3]+. J. Am. Chem. Soc. 2001; 123:3135-36.

Antony AC, Kane MA, Portillo RM, Elwood PC, Kolhouse JF. Studies of the role of a particulate folate-binding protein in the uptake of 5-methyltetrahydrofolate by cultured human KB cells. J. Biol. Chem. 1985; 260:4911-17.

Dixon KH, Mulligan T, Chung KN, Elwood PC, Cowan KH. Effects of folate receptor expression following stable transfection into wild type and methotrexate transport-deficient ZR-75-1 human breast cancer cells. J. Biol. Chem. 1992; 267:24140-47.

Ladino CA, Chari RVJ, Bourret LA, Kedersha NL, Goldmacher VS. Folate-maytansinoids: target-selective drugs of low molecular weight. Int. J. Cancer 1997; 73:859-64.

Mathias CJ, Wang S, Lee RJ, et al. Tumor-selective radiopharmaceutical targeting via receptor-mediated endocytosis of gallium-67-deferoxamine-folate. J. Nucl. Med. 1996; 37:1003-08.

Li Y, Looney GA, Hurwitz A. Effects of morphine on methotrexate disposition in mice. Clin. Exp. Pharmacol. Physiol. 2004; 31:267-70.

Pritchard DM, Bower L, Potten CS, Jackman AL, Hickman JA. The importance of p53-independent apoptosis in the intestinal toxicity induced by raltitrexed (ZD1694, Tomudex): genetic differences between BALB/c and DBA/2 mice. Clin. Cancer Res. 2000; 6:4389-95.

Hughes A, Calvert P, Azzabi A, et al. Phase I clinical and pharmacokinetic study of pemetrexed and carboplatin in patients with malignant pleural mesothelioma. Journal of Clinical Oncology 2002; 20:3533-44.

Aherne GW, Ward E, Lawrence N, et al. Comparison of plasma and tissue levels of ZD1694 (Tomudex), a highly polyglutamatable quinazoline thymidylate synthase inhibitor, in preclinical models. Br. J. Cancer 1998; 77:221-26.

Schibli R, Schwarzbach R, Alberto R, et al. Steps toward high specific activity labeling of biomolecules for therapeutic application: preparation of precursor [188Re(H2O)3(CO)3]+ and synthesis of tailor-made bifunctional ligand systems. Bioconjugate Chem. 2002; 13:750-56.

Cristina Muller et al., "Prospects in Folate Receptor-targeted Radionuclide Therapy", Frontiers in Oncology, vol. 3, Article 249, Sep. 2013, pp. 1-10.

Carla J. Mathias et al., "Receptor-Meditated Targeting of 67Ga-Deferoxamine-Folate to Folate-Receptor-Positive Human KB Tumor Xenografts", Nuclear Medicine & Biology, vol. 26, 1999, pp. 23-25.

Josefine Reber et al., "Lu-EC0800 Combined with the Antifolate Pemetrexed: Preclinical Pilot Study of Folate Receptor Targeted Radionuclide Tumor Therapy", Molecular Cancer Therapeutics, vol. 12, No. 11, Nov. 2013, pp. 2436-2445.

Cristina Muller et al., "Premetrexed Improved Tumor Selectivity of 111 In-DTPA-Folate in Mice with Folate Receptor-Positive Ovarian Cancer", J. Nucl. Med., vol. 49, 2008, pp. 623-629.

Moller et al., "Isostructural folate conjugates radiolabeled with the matched pair 99mTc1188 Re: a potential strategy for diagnosis and therapy of folate receptor-positive tumors", Nuclear Medicine and Biology, vol. 34, (2007) 595-601.

* cited by examiner

METHOD FOR CELL-SPECIFIC TARGETING

FIELD OF THE INVENTION

The present invention relates to a method for selective protection of human healthy, normal tissue expressing folate receptors while enhancing targeting of a cell or populations of cells expressing folate-receptors of the type alpha, beta and gamma or activated (but not resting) synovial macrophages, and its use in diagnostic and therapeutic medical applications, for example diagnostic imaging, radiotherapy, boron neutron capture therapy, chemotherapy. In particular selective protecting is achieved by simultaneous or sequential administration of an antifolate with a folate- or pteroate-conjugate comprising one or more effector moieties.

BACKGROUND OF THE INVENTION

Cell-specific targeting for delivery of effector moieties such as diagnostic or therapeutic agents is a widely researched field and has led to the development of non-invasive diagnostic and/or therapeutic medical applications. In particular in the field of nuclear medicine procedures and treatments, which employ radioactive materials emitting electromagnetic radiations as γ-rays or photons or particle emitting radiation (e.g. alpha, beta, Auger-electrons), selective localization of these radioactive materials in targeted cells or tissues is required to achieve either high signal intensity for visualization of specific tissues, assessing a disease and/or monitoring effects of therapeutic treatments, or high radiation dose, for delivering adequate doses of ionizing radiation to a specified diseased site, without the risk of radiation injury in other e.g. healthy tissues. It is thus of crucial interest to determine and assess cell-specific and in particular tumour-selective structures such as receptors, antigens and the like which can be specifically targeted by the respective biological vehicles.

The folate receptor (FR) has been identified as one of these structures. The FR is a high-affinity ($K_D < 10^{-9}$ M) membrane-associated protein. In normal tissues and organs FR-expression is highly restricted to only a few organs (e.g. kidney, lungs, choroids plexus, and placenta), where it largely occurs at the luminal surface of epithelial cells and is therefore not supplied with folate in the circulation. The FR-alpha is frequently overexpressed on a wide variety of specific cell types, such as epithelial tumours (e.g. ovarian, cervical, endometrial, breast, colorectal, kidney, lung, nasopharyngeal), whereas the FR-beta is frequently overexpressed in leukaemia cells (approx. 70% of acute myelogenous leukaemia (AML) are FR-beta positive). Both may therefore be used as a valuable tumour marker for selective tumour-targeting (Elnakat and Ratnam, Adv. Drug Deliv. Rev. 2004; 56:1067-84). In addition it has recently been discovered that activated (but not resting) synovial macrophages in patients diagnosed with rheumatoid arthritis possess a functionally active FR-beta. Therefore activated macrophages can be selectively targeted with folate conjugates in arthritic joints, a capability that opens possibilities for the diagnosis and treatment of rheumatoid arthritis (Paulos et al, Adv. Drug Deliv. Rev. 2004; 56:1205-17). Folic acid and its derivatives have thus been intensively studied over the past 15 years as targeting agents for the delivery of therapeutic and/or diagnostic agents to cell populations bearing folate receptors in order to achieve a selective concentration of therapeutic and/or diagnostic agents in such cells relative to normal cells. Various probes have been conjugated to folic acid and (pre)clinically evaluated, including folate radiopharmaceuticals (Leamon and Low, Drug Discov. Today 2001; 6:44-51), folate-conjugates of chemotherapeutic agents (Leamon and Reddy, Adv. Drug Deliv. Rev. 2004; 56:1127-41; Leamon et al, Bioconjugate Chem. 2005; 16:803-11), proteins and protein toxins (Ward et al., J. Drug Target. 2000; 8:119-23; Leamon et al, J. Biol. Chem. 1993; 268:24847-54; Leamon and Low, J. Drug Target. 1994; 2:101-12), antisense oliconucleotides (Li et al, Pharm. Res. 1998; 15:1540-45; Zhao and Lee, Adv. Drug Deliv. Rev. 2004; 56:1193-204), liposomes Lee and Low, Biochim. Biophys. Acta-Biomembr. 1995; 1233:134-44; Gabizon et al, Adv. Drug Deliv. Rev. 2004; 56:1177-92), MRI contrast agents (Konda et al, Magn. Reson. Mat. Phys. Biol. Med. 2001; 12:104-13) etc.

However, apart from specific uptake of folate-conjugates in tumours, substantial and specific accumulation was also observed in kidneys because of considerable expression of FRs in proximal tubule cells of the renal tissue (Mathias et al, J. Nucl. Med. 1998, 39:1579-85; Mathias and Green, Nucl. Med. Biol. 1998, 25:585-87; Mathias and Green, J. Nucl. Med. 2000, 41:1113; Siegel et al, J. Nucl. Med. 2003, 44:700-07; Leamon et al, Bioconjugate Chem. 2002, 13:1200-10; Reddy et al, J. Nucl. Med. 2004, 45:857-66; Mathias et al, Bioconjugate Chem. 2000, 11:253-57; Trump et al, Nucl. Med. Biol. 2002, 29:569-73; Wang et al, Bioconjugate Chem. 1997, 8:673-79). This issue severely limit the use of currently known folate-mediated targeting methods in various medical applications and in particular the use of therapeutic folate/pteroate-conjugates radiolabeled with particle-emitting radioisotopes ($\beta^-$ or $\alpha$), since application of high radioactivity in order to achieve a cytotoxic radiation dose in tumour cells would consequently comprise the risk of radiation injury in sensitive renal tissue. Therefore, FR tumour-targeting has not been exploited for its use in radiotherapy so far.

In view of the above limitations, there is clearly a need for appropriate targeting methods which show high selectivity of the folate/pteroate-conjugates to the targeted sites and efficiency (and thus adequate safety) for their use in various medical applications.

Applicants have now found that these disadvantages can be overcome by simultaneous or sequential administration of antifolates and folate/pteroate-conjugates, which led to a drastic increase in tumour selectivity of the folate-based radiopharmaceutical (i.e. increase of the tumour-to-kidney ratio of radioactivity).

SUMMARY OF THE INVENTION

The present invention relates in a first aspect to a method for selective targeting of one or more effector moieties to a cell or population of cells expressing a folate-receptor and its use in diagnostic and therapeutic medical applications, such as diagnostic imaging, radiotherapy, boron neutron capture therapy, chemotherapy. More particularly targeting of said cell or population of cells is achieved by simultaneous or sequential administration of an antifolate and a folate/pteroate-conjugate comprising said one or more effector moieties.

In a preferred embodiment said method comprises the steps of administering an antifolate in effective amounts, followed by administering a folate/pteroate-conjugate comprising said one or more effector moieties in effective amounts. Alternatively said method comprises the steps of administering a folate/pteroate-conjugate comprising said one or more effector moieties in effective amounts, followed by administering an antifolate in effective amounts.

Preferably said cell or population of cells is a tumour cell or a population of tumour cells including leukaemia cells, or activated macrophages in rheumatoid arthritis.

In a particular embodiment the folate- or pteroate-conjugate comprises a folate, pteroate or a derivative thereof which is linked directly or through a spacer to said one or more effector moieties.

Typical effector moieties may include one or more diagnostic or therapeutic agents. In one particular embodiment of the invention, the effector moiety contains one or more macrocyclic or non-macrocyclic metal chelating ligand radicals that are optionally chelated to paramagnetic, super-paramagnetic, radioactive, or non-radioactive metals which may be detectable by imaging means for diagnostic purposes or which may provide a therapeutic or radiotherapeutic effect. In other embodiments the effector moiety may also include a therapeutic agent selected from any other biologically active compound.

In a particular embodiment the folate, pteroate or derivative thereof is selected from folic acid, pteroic acid, folinic acid, pteropolyglutamic acid, and folate receptor-binding pteridines such as tetrahydropterins, dihydrofolates, tetrahydrofolates, and their deaza and dideaza analogs.

In another particular embodiment the antifolate is an inhibitor of folate-dependent enzymes such as e.g. the dihydrofolate reductase (DHFR), thymidylate synthase (TS), GARformyltransferase or AICA formyltransferase, preferably selected from the group of compounds comprising Methotrexate, raltitrexed, pemetrexed, trimetrexate, edatrexate, lometrexol, nolatrexed and aminopterin.

Thus in a specific embodiment, the present invention provides a method for selective targeting of one or more effector moieties to a cell or population of cells expressing a folate-receptor, wherein said folate- or pteroate-conjugate is a compound of formula (I)

$$F—S—E \qquad (I)$$

wherein

F represents a folate, pteroate or derivative thereof; —
S represents a single bond or a spacer, and
E is either a pharmaceutically active agent, a non-metallic radionuclide, or a complex C•M, wherein C represents a metal-chelating ligand and M represents a metallic radioisotope chelated by said metal-chelating ligand C (FIG. 1).

In a further aspect, the present invention provides a method for diagnostic imaging of a cell or population of cells expressing a folate-receptor, said method comprising the steps of: administering an antifolate in effective amounts, followed by administering a folate/pteroate-conjugate comprising a diagnostic agent in effective amounts to allow binding) to occur, and obtaining a diagnostic image of said cell or population of cells using Nuclear Medicine (single photon emission tomography (SPECT), or positron emission tomography (PET)) or Magnetic Resonance imaging techniques (FIG. 2). Consequently improved target-to-non-target ratios can be achieved enabling the more precise localisation of malignant cell populations and reducing unwanted dose burden to healthy tissue and organs (FIG. 3-6). Alternatively said method comprises the steps of administering a folate/pteroate-conjugate comprising a diagnostic agent in effective amounts, followed by administering an antifolate in effective amounts. More alternatively said method comprises administering a folate/pteroate-conjugate comprising a diagnostic agent in effective amounts, simultaneously with an antifolate in effective amounts.

In yet a further aspect, the present invention provides a method for radiotherapy comprising the steps of: administering an anti-folate in effective amounts, followed by administering a folate/pteroate-conjugate comprising a radiotherapeutic agent in effective amounts and after localization of said folate/pteroate-conjugate in the desired tissues, subjecting the tissues to irradiation to achieve the desired therapeutic effect in the targeted but not healthy tissue and organs. Alternatively said method comprises the steps of administering a folate/pteroate-conjugate comprising a radiotherapeutic agent in effective amounts, followed by administering an antifolate in effective amounts. More alternatively said method comprises administering a folate/pteroate-conjugate comprising a radiotherapeutic agent in effective amounts, simultaneously with an anti-folate in effective amounts.

In a further aspect, the present invention provides a method for chemotherapy comprising the steps of: administering to a subject in need thereof an antifolate in effective amounts, followed by administering a folate/pteroate-conjugate comprising a chemotherapeutic agent in effective amounts to achieve the desired diagnostic and therapeutic effect. Alternatively said method comprises the steps of administering a folate/pteroate-conjugate comprising a chemotherapeutic agent in effective amounts, followed by administering an antifolate in effective amounts. More alternatively said method comprises administering a folate/pteroate-conjugate comprising a chemotherapeutic agent in effective amounts, simultaneously with an antifolate in effective amounts.

In yet a further aspect the present invention provides a kit, preferably a multi-vial kit, that contains in separate vials all of the components needed for co administration of antifolate and folate/pteroate-conjugate.

Other features and advantages of the invention will be apparent from the following detailed description thereof and from the claims.

DETAILED DESCRIPTION OF THE INVENTION

Figure 1:
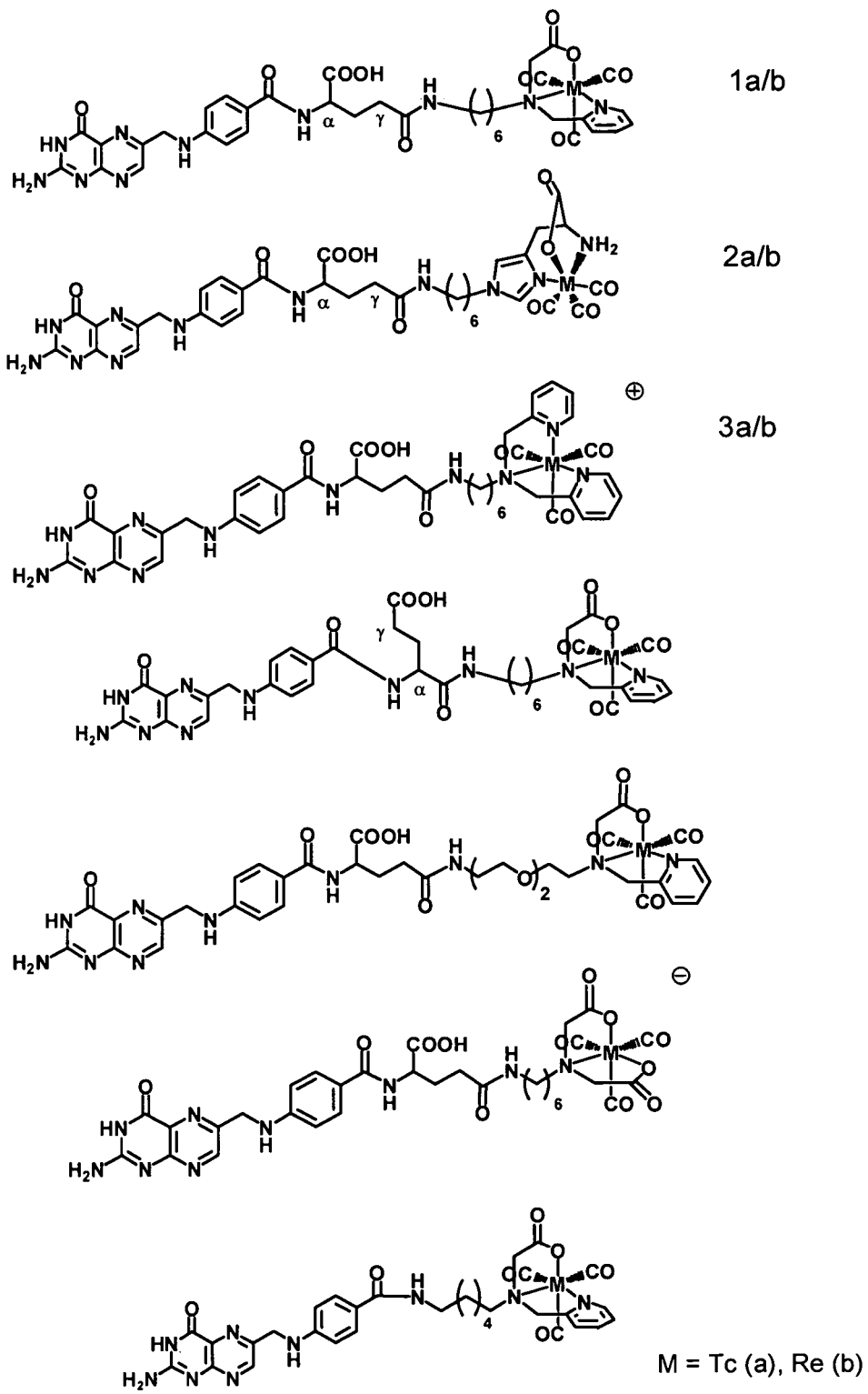
FIG. 1. Structure of radiotracers.
Figure 2:
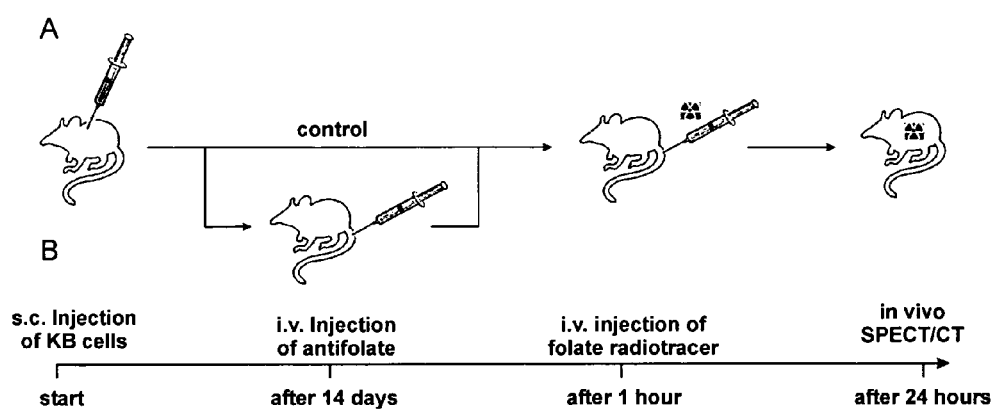
FIG. 2. Procedure of the pre-treatment of mice with antifolates and administration of radiotracers.

The present invention provides in a first aspect a method of selective targeting of one or more effector moieties to a cell or population of cells expressing a folate-receptor. More particularly targeting of said cell or population of cells is achieved by simultaneous or sequential administration of an antifolate and a folate/pteroate-conjugate comprising said one or more effector moieties.

In particular the present invention provides a method for selective targeting of one or more effector moieties to a cell or population of cells expressing a folate-receptor, preferably tumour cells or activated macrophages, comprising the steps of: administering an antifolate in effective amounts, followed by administering a folate/pteroate-conjugate comprising said one or more effector moieties. Alternatively said method comprises the steps of administering a folate/pteroate-conjugate comprising said one or more effector moieties in effective amounts, followed by administering an antifolate in effective amounts. More alternatively said method comprises administering a folate/pteroate-conjugate comprising said one or more effector moieties in effective amounts, simultaneously with an antifolate in effective amounts.

It has been shown, that such a method is particularly useful in various diagnostic and therapeutic medical applications, wherein folate/pteroate-conjugates are used as a delivery vehicle of effector moieties in folate-mediated targeting of cells expressing the folate-receptor.

In a specific embodiment such cells are epithelial tumour cells (e.g. ovarian, endometrial, breast, colorectal, kidney, lung, nasopharyngeal tumour cells), leukaemia cells or activated macrophages in rheumatoid arthritis.

An antifolate for use in the present invention is any compound that is capable of interfering at various stages of folate metabolism, such as for example a direct inhibitor of the dihydrofolate reductase (DHFR), thymidylate synthase (TS), GARformyltransferase or AICA formyltransferase and/or a direct inhibitor of at least one of the folate-dependent enzymes of de novo purine synthesis. Such compounds include in particular methotrexate (MTX), raltitrexed (RTX), pemetrexed (PMX), trimetrexate, edatrexate, lometrexol, nolatrexed, aminopterin, and other thymidylate synthase inhibitors. It is understood that other antifolate drugs known to those skilled in the art or currently in development (see for example U.S. Pat. No. 5,747,499) including newer antifolates which may inhibit more than one pathway in folate metabolism, that have improved delivery, or that inhibit other targets in folate metabolism can also be used in the present invention.

The term "folate/pteroate" as used in the present invention includes a folate, pteroate or derivative thereof and comprises in particular folic acid, pteroic acid, folinic acid, pteropolyglutamic acid, and folate receptor-binding pteridines such as tetrahydropterins, dihydrofolates, tetrahydrofolates, its 5-substituted derivatives such as 5-formyltetrahydrofolic acid or 5-methyltetrahydrofolic acid, its 10-substituted derivatives such as 10-formyltetrahydrofolic acid, its 5,10 substituted or 5,10-bridged derivatives such as 5,10-methylenetetrahydrofolic acid or 5,10-methenyltetrahydrofolic acid, their deaza and dideaza analogs and all salts, esters and polyglutamated forms thereof. The terms "deaza" and "dideaza" analogs refer to well known analogs having a carbon atom substituted for one or two nitrogen atoms in the naturally occurring folic acid structure. For example, the deaza analogs include the 1-deaza, 3-deaza, 5-deaza, 8-deaza, and 10-deaza analogs. The dideaza analogs include, for example, 1,5 dideaza, 5,10-dideaza, 8,10-dideaza, and 5,8-dideaza analogs. The term "esters" refers to well known aliphatic or aromatic esters having one or more glutamic acid moiety esterified.

An effector moiety for use in the present invention generally comprises a diagnostic or therapeutic agent:

Diagnostic agents suitable for use in the present invention include any compound that is capable of being detected in vivo after administration to the targeted cells. Preferred agents include electron dense materials, magnetic resonance imaging agents and radiopharmaceuticals. Therapeutic agents suitable for use in the present invention include any compound that is capable of achieving the desired therapeutic efficacy at the targeted site. Typical therapeutic agents include non-metallic and complexed metallic radionuclides as well as other pharmacologically active agents, in particular chemotherapeutic agents.

In one embodiment of the invention, the effector moiety represents one or more non-metallic radionuclides (i.e. non-metallic radioisotopes), which may be detectable by imaging means for diagnostic purposes or which may provide a therapeutic or radio-therapeutic effect. Specifically, the non-metallic radionuclide can be a non-metallic paramagnetic atom (e.g. Fluorine-19); or non-metallic positron emitting radionuclide (e.g. Carbon-11, Fluorine-18, Iodine-124 or Bromine-76) or a nonmetallic gamma emitting radionuclide such as Iodine-123 or Iodine-131. Preferred radioactive isotopes useful in radiographic imaging or radiotherapy including are $^{11}C$, $^{18}F$, $^{123}I$, $^{124}I$, $^{125}I$, and $^{131}I$, particularly preferred for diagnostic purposes is $^{123}I$, and for therapeutic purposes $^{131}I$.

In another embodiment of the invention, the effector moiety contains one or more macrocyclic or non-macrocyclic metal chelating ligand radicals that are optionally chelated to paramagnetic, super-paramagnetic, radioactive, or non-radioactive metals which may be detectable by imaging means for diagnostic purposes or which may provide a therapeutic or radiotherapeutic effect (see for example also "Radionuclides for Therapy", ed. P. Schubiger and P. H. Hasler, 1986). The structure of these chelating ligands and the respective metals may vary depending on the desired use. For example conjugates that include paramagnetic or superparamagnetic metals are useful as diagnostic agents in MR imaging applications. Paramagnetic metals that may be used in the conjugates include, but are not limited to, chromium (III), manganese (II), iron (II), iron (III), cobalt (II), nickel (II), copper (II), praseodymium (III), neodymium (III), samarium (III), gadolinium (III), terbium (III), dysprosium (III), holmium (III), erbium (III), and ytterbium (III). Chromium (III), manganese (II), iron (III), and gadolinium (III).

Conjugates that include radioactive metals are useful in radiographic imaging or radiotherapy: Preferred radioisotopes include $^{99m}Tc$, $^{51}Cr$, $^{67}Ga$, $^{68}Ga$, $^{111}In$, $^{168}Yb$, $^{175}Yb$, $^{140}La$, $^{90}Y$, $^{88}Y$, $^{153}Sm$, $^{166}Ho$, $^{165}Dy$, $^{166}Dy$, $^{62}Cu$, $^{64}Cu$, $^{67}Cu$, $^{97}Ru$, $^{103}Ru$, $^{186}Re$, $^{188}Re$, $^{203}Pb$, $^{211}Bi$, $^{212}Bi$, $^{213}Bi$, $^{214}Bi$, $^{105}Rh$, $^{109}Pd$, $^{117m}Sn$, $^{149}Pm$, $^{161}Tb$, $^{177}Lu$, $^{198}Au$, and $^{199}Au$. The choice of metal will be determined based on the desired therapeutic or diagnostic application.

For diagnostic purposes the preferred radionuclides include $^{111}In$, $^{67}Ga$, $^{68}Ga$, $^{99m}Tc$, most preferably $^{99m}Tc$. For therapeutic purposes, the preferred radionuclides include $^{64}Cu$, $^{90}Y$, $^{105}Rh$, $^{117m}Sn$, $^{149}Pm$, $^{53}Sm$, $^{161}Tb$, $^{166}Dy$, $^{166}Ho$, $^{175}Yb$, $^{177}Lu$, $^{186/188}Re$, and $^{199}Au$, most preferably $^{67}Cu$, $^{177}Lu$ and $^{186/188}Re$.

Suitable metal chelating ligands that have been reported in the literature may include for example multidentate chelators, i.e. bi-, tri, and tetradentate chelators, that bind to radionuclide metals through nitrogen and/or oxygen and/or sulphur metal coordinating atoms (see for example, U.S. Pat. Nos. 6,143,274, 6,093,382; EP 0 629 617, WO 03/077727, EP 0 772 628 as well as Liu and Edwards, Chem. Rev. 1999, 99, 2235-2268 and references therein). The effector moiety may also include complexes containing ligand atoms that are not donated to the metal in a multidentate array. These include for example the boronic acid adducts of technetium and rhenium dioximes (see for example EP 0 452 858).

It is understood that the nature of the chelating ligand depends naturally on the metal of choice. Thus for example in the case of lanthamides such as Sm, Eu, Gd, Ho or Lu, or transition metals such as Cu, Co, Ga, Y, In, macrocyclic tetraaza ligands of the DOTA type (DOTA=1,4,7,10-tetraaza-cyclododecane-N,N',N'',N'''-tetra acetic acid) are applicable. For transition metals such as Tc and Re preferred chelating ligands may include polydentate nitrogen, sulphur, phosphorous and oxygen chelating systems such as EDTA, DTPA and derivatives (as described in the literature cited hereinabove), or bi- and tridentate ligands such as iminodiacetic acid, picolylaminomonoacetic acid, bis(pyridylmethyl)amine, histidine and pseudohistidine chelators, more preferably tridentate ligands carrying terminal pyridyl groups such as picolylaminomonoacetic acid, bis(pyridylmethyl)amine or imidazol groups such as histidine.

In another embodiment of the invention, the effector moiety contains a substance that emits short-range radiation when it is irradiated with neutrons, otherwise known as Neutron Capture Therapy. Preferably, the effector moiety comprises Boron-10 as a therapeutic agent for Boron Neutron Capture Therapy (BNCT), while other substances, such as Gadolinium-157 may also be contemplated.

In yet another embodiment the therapeutic agents which are contemplated as effector moieties herein, include also any other known biologically active agents capable of modulating or otherwise modifying cell function. Such pharmacologically active compounds may thus include, but are not limited to:

naturally occurring compounds such as peptides, oligopeptides, proteins, glycoproteins, antigens and antibodies thereto, amino acids, nucleotides, oligonucleotides, polynucleotides, lipids, phospholipids and their well-known and biologically functional analogs and derivatives; toxins such as aflatoxin, digoxin, xanthotoxin; antibiotics such as cephalosporins, penicillin, and erythromycin; antiviral agents; antimicrobial agents; H-2 antagonists such as nizatidine, cimetidine, famotidine, and ranitidine; therapeutic agents involved in cancer treatment, which include chemotherapeutics in general (e.g. fluorouracil), and more specifically alkylating agents (e.g. carmustine, cisplatin, carboplatin), antiangiogenesis drugs (e.g. thalidomide, heparin), anti-cancer agents, such as derivatized paclitaxel (TAXOL (L)), docetaxel, vinca alkaloids such as vincristine, vinblastine, dolostatins, daunomycin, doxorubicin, bleomycin, halichondrins, etc., antisense therapeutics, gene therapeutics, antibody therapeutics, anti-cytokine therapeutics (e.g. interleukin-12, low molecular weight heparin), antimetabolite therapeutics (e.g. gemcitabine, hydrioxyurea), DNA adduct forming drugs (e.g. Oxaliplatin), radiotherapeutics (as mentioned hereinabove) and others (for an extensive listing of chemotherapeutic agents useful in neoplastic disease see for example Goodman & Gilman's The Pharmacological Basis of Therapeutics, 60th Ed., 1980, MacMillan Publ. Co., New York, pp. 1252-1254, The Merck Index, 11th Ed. 1989, which are incorporated herein by reference); or any other biologically active molecule that can form a complex with a folate or analog thereof, by direct or indirect conjugation of the agent with a folate or analog thereof without interfering with or disrupting the binding of the folate or derivative thereof with its receptor on the cell.

A folate/pteroate-conjugate for use in the present invention is a folate, pteroate or derivative thereof as defined hereinabove comprising one or more effector moiety, such that the folate/pteroate-portion of said conjugate is still able to interact with the folate binding receptor present on the targeted cells.

In a specific embodiment a folate/pteroate-conjugate comprises one folate, pteroate or derivative thereof linked to one effector moiety.

Typically, the effector moiety of choice may be linked to the folate or pteroate either directly through hydrogen, ionic, or covalent bonding using well known coupling techniques or indirectly, whereby the effector moiety is spaced by a linker, spacer or bridging molecule or is associated with e.g. a lipid vesicle, such as a liposome.

In a preferred embodiment the conjugate is formed by covalent bonding of a folate or pteroate to an effector moiety of choice, i.e. through the formation of e.g. amide, ester, imino bonds and the like between the respective functional groups present on the folate/pteroate and effector moiety. Preferably the folate/pteroate-conjugate is formed through linking of the effector moiety of choice to the alpha, gamma or both the alpha and gamma carboxylate of the glutamate moiety of the folate molecule and the pteroate-conjugate is formed through linking of the effector moiety of choice directly to the carboxylate group of the pteroate molecule. Thus, for example, said alpha and/or gamma carboxylate of the folate or the carboxylate group of the pteroate can be activated using, for example, carbonyldiimidazole or standard carbodiimide coupling reagents such as 1-ethyl-3-(3-dimethylaminopropyl) carbodiimide (EDC) and thereafter reacted with a nucleophilic group present on the effector moiety, such as an hydroxy, amino, hydrazo, or thiol group, to form the respective conjugate coupled through an ester, amide, or thioester bond. Depending on the nature and intended use of the effector moiety, the nature of the covalent bonding between the folate/pteroate moiety and the effector moiety may differ and may be stable or biologically labile. The latter, i.e. biologically labile bonds is preferred where release of the effector moiety is desired, for example in case of a therapeutic agent having higher functionality in its free state compared to its conjugated state. Biologically labile linkages include imino bonds (—C=N—), activated ester bonds, such as —COOCH$_2$O— or —COOCH(CH$_3$)O—, hydrazone bonds or disulfide bonds and the like.

In another embodiment the conjugate is formed through hydrogen bonding, as it is occurring for example between complementary strands of nucleic acids. Thus complex formation occurs through hydrogen bonding between an effector moiety, which in this case is a nucleic acid, and a folate or pteroate conjugated to an oligonucleotide which is complementary to at least a portion of said nucleic acid (see for example U.S. Pat. No. 6,861,514).

In other embodiments the effector moiety may be spaced by a spacer S, which includes, but is not limited to alkyl chain-linkers, polyethyleneglycole —(CH$_2$—CH$_2$—O—)$_n$ linkers, ω-aminoalkoxy linkers, ω-aminoalkylamino linkers, heterobifunctional linkers, homobifunctional linkers, peptidic linkers, linear or dendritic or carbohydrate linkers and the like.

In yet other embodiments, the effector moiety also be associated with a phospholipid moiety, which may be part of a liposome. Artificially generated phospholipid vesicles are known for their use as carriers for introducing membrane-impermeable substances into cells, including for example radionuclides (see for example U.S. Pat. No. 6,592,843) of chemotherapeutics. In accordance with the present invention, suitable liposome-forming phospholipids can be conjugated to a folate through, for example, headgroup functional groups such as hydroxy and amino groups. The resulting folate-phospholipid complex is then used itself or in combination with unmodified phospholipids to form liposomes containing agents capable of modulating or otherwise modifying cell functions. The resulting folate- or pteroate-liposome conjugates present may be used in accordance with the present invention to promote delivery of the liposome-contained one or more effector moieties into the cell. One readily available phospholipids that can be used in accordance with the above-described method is for example phosphatidylethanolamine. That phospholipid can be conveniently complexed using art-recognized procedures with a folate or pteroate to form a folate- or pteroate-phospholipid complex. This complex can be combined with other phospholipids, for example, phosphatidylcholine and that mixture can be used to form liposomes containing effector moieties to be delivered to the targeted cells.

In a particular embodiment the folate/pteroate-conjugate is a compound of formula (I)

$$F-S-E \qquad (I)$$

wherein
F is a folate, pteroate or derivative thereof, S is a single bond or a spacer, and E is an effector moiety, such as a diagnostic or a therapeutic agent and in particular a non-metallic radionuclide or a complex C•M, wherein C represents a metal-chelating ligand, and M represents a metallic radionuclide chelated by said metal-chelating ligand C, or a pharmacologically active agent.

The disclosures of all of the referenced citations hereinabove are incorporated by reference in their entirety.

The present invention provides a method which dramatically increases the selective targeting of cells expressing the folate receptor, while abolishing the accumulation in untargeted tissue, in particular renal tissue, which is typically observed with folate/pteroate conjugates which are excreted via kidneys previously described targeting methods. Thus the method of the present invention may be employed in various medical applications where high selectivity is required, for example Nuclear Medicine Imaging Techniques (radiodiagnostic imaging) using γ-emitting radionuclides as effector moieties; Magnetic Resonance Imaging (MRI) Techniques using chelated superparamagnetic or paramagnetic metals as effector moieties; in particular radiotherapy using chelated radioactive alpha or beta-emitting metals as effector moieties; and chemotherapy using chemotherapeutic agents as effector moieties. The subject undergoing diagnostic imaging or treatment according to the present invention is preferably a mammalian subject, i.e. an animal or human.

Thus in a further aspect the present invention provides a method for the diagnosis of the presence and/or status of a disease state, or a method for monitoring of the treatment of a disease.

In a particular embodiment, the present invention provides a method for diagnostic imaging of a cell or population of cells expressing a folate-receptor, said method comprising the steps of: administering an antifolate in effective amounts, followed by administering a folate/pteroate-conjugate comprising a diagnostic agent in effective amounts to allow binding to occur, and obtaining a diagnostic image of said cell or population of cells using imaging techniques such as Nuclear Medicine Imaging Techniques or Magnetic Resonance Imaging Techniques. Alternatively said method comprises the steps of administering a folate/pteroate-conjugate comprising a diagnostic agent in effective amounts, followed by administering an antifolate in effective amounts. More alternatively said method comprises administering a folate/pteroate-conjugate comprising a diagnostic agent in effective amounts, simultaneously with an antifolate in effective amounts.

In another embodiment the present invention provides a method for radiotherapy comprising the steps of: administering to a subject in need thereof an antifolate in effective amounts, followed by administering a folate/pteroate-conjugate comprising a radiotherapeutic agent in effective amounts to allow binding to occur, and after localization of said folate/pteroate-conjugate in the desired tissues, subjecting the tissues to irradiation to achieve the desired therapeutic effect. Alternatively said method comprises the steps of administering a folate/pteroate-conjugate comprising a radiotherapeutic agent in effective amounts, followed by administering an antifolate in effective amounts. More alternatively said method comprises administering a folate/pteroate-conjugate comprising a radiotherapeutic agent in effective amounts, simultaneously with an antifolate in effective amounts.

In yet another embodiment the present invention provides a method for chemotherapy comprising the steps of: administering to a subject in need thereof an antifolate in effective amounts, followed by administering a folate/pteroate-conjugate comprising a chemotherapeutic agent in effective amounts to achieve the desired therapeutic effect. Alternatively said method comprises the steps of administering a folate/pteroate-conjugate comprising a chemotherapeutic agent in effective amounts, followed by administering an antifolate in effective amounts. More alternatively said method comprises administering a folate/pteroate-conjugate comprising a chemotherapeutic agent in effective amounts, simultaneously with an antifolate in effective amounts.

In yet a further embodiment the present invention provides a method for boron neutron therapy comprising the steps of: administering to a subject in need thereof an antifolate in effective amounts, followed by administering a folate/pteroate-conjugate comprising Boron-10 in effective amounts, and after localization of said folate/pteroate-conjugate in the desired tissues, subjecting the tissues to irradiation to achieve the desired therapeutic effect. Alternatively said method comprises the steps of administering a folate/pteroate-conjugate comprising Boron-10 in effective amounts, followed by administering an antifolate in effective amounts. More alternatively said method comprises administering a folate/pteroate-conjugate comprising Boron-10 in effective amounts, simultaneously with an antifolate in effective amounts.

In a specific embodiment the antifolate and folate/pteroate-conjugate are administered sequentially, i.e. at least 1 minute apart. It is understood that the administration regimen depends on the administration route of choice, the subject to be treated, etc. For example intravenous administration may require less time for efficient binding to occur than oral administration. Thus in case of pre-treatment, the antifolate may be for example administered up to 24 hours, preferably up to 12 hours, more preferably up to 6 hours and most preferably up to 4 hours prior to administration of the folate/pteroate-conjugate. In case of post-treatment the antifolate may be for example administered up to 4 hours, preferably up to 1 hour or less after administration of the folate/pteroate-conjugate. A skilled person will understand that the sequence and time intervals of administration are dependent on the specific circumstances.

According to in vivo experiments with mice administration of the antifolate revealed to be most favourable one hour prior to the administration of the folate/pteroate-conjugate. However the sequence of administration can be different in humans.

It is understood that antifolate and/or folate- or pteroate-conjugate may be administered alone or in combination with pharmaceutically acceptable carriers, the proportion of which is determined by the chemical nature of the effector moiety conjugated to the folate or pteroate, chosen route of administration and standard pharmaceutical practice. Suitable administration routes include intravenous (bolus or continuously), intramuscular or intraperitoneal routes, in a physiologically acceptable medium, such as saline or water that is buffered or pH adjusted using physiologically acceptable salts or buffers well-known in the art. Likewise depending on the nature and intended use of the effector moiety of choice conjugated to the folate or pteroate a therapeutically effective amount can vary widely.

Suitable dosages may be selected based on the desired use, such as to produce a diagnostic image of an organ or to achieve a desired therapeutic effect, yet dosage levels are considerably lower compared to currently employed methods due to the high selectivity and efficient delivery of the methods of the present invention and thus high localization of the effector moiety in the targeted tissue.

In yet a further aspect the invention provides a kit, for example a multi-vial kit, that contains all of the components needed for coadministration of antifolate and folate/pteroate-conjugate. In one embodiment, the kit, for example a multivial kit, comprises in one vial the folate/pteroate-conjugate and in a further vial the antifolate. Thus in a specific embodiment the invention provides a kit for diagnostic imaging of a cell or population of cells expressing a folate-receptor, said kit comprising an antifolate in effective amounts, and folate- or pteroate-conjugate comprising a diagnostic agent, such as for example at least one paramagnetic, super-paramagnetic, or radioactive metallic radionuclide, in effective amounts. Depending on the nature of the folate/pteroate-conjugate further vials may be necessary, i.e. for radiodiagnostic or radiotherapeutic applications it is convenient to prepare the complexes of the present invention at, or near, the site where they are to be used. Thus, separate vials may be used to store the components for in situ generation of the labile complex. The contents of the vials are preferably lyophilized. Each vial may contain additional additives to improve e.g. radiochemical purity and stability of the final product, or to aid in the production of the kit. The amounts contained in the vials may be chosen such that they are sufficient for application in Imaging techniques such as Nuclear Medicine or Magnetic resonance techniques.

The following examples are provided to illustrate further the method of the present invention.

EXAMPLES

Example 1

Materials and Methods. The synthesis of the picolylamine monoacetic acid (PAMA)-folate-conjugate was performed as described in (Müller et al, J. Organomet. Chem. 2004, 689: 4712-21). Precursor $[^{99m}Tc(CO)_3(OH_2)_3]^+$ was prepared using the Isolink™-kit (Mallinckrodt-Tyco, Petten, the Netherlands) (Alberto et al, J. Organomet. Chem. 1995, 492:217-24; Alberto et al, J. Am. Chem. Soc. 2001; 123:3135-36). $[Na][^{99m}TcO_4]$ was eluted from a $^{99}Mo/^{99m}Tc$-generator (Mallinckrodt-Tyco, Petten, the Netherlands) with a 0.9% saline solution. $[Na][^{188}ReO_4]$ was eluted from a $^{188}W/^{188}Re$-generator (Oak Ridge National Laboratories, Oak Ridge, Tenn.). Injection solutions of methotrexate (Amersham Life Science) were prepared with phosphate buffered saline (PBS, pH 7.4) followed by sterile flirtation. The injection solutions of Tomudex® (ralitrexed) and Alimta® (pemetrexed) were prepared according to the package instructions with aqua ad injectabilia or NaCl 0.9% respectively. KB cells (CCL-17) were purchased from ATCC (American Type Culture Collection, Manassas, USA) and KB-V1 (ACC 149) were purchased from DSMZ (German Collection of Microorganisms and Cell Cultures, Braunschweig, Germany) IGROV-1 cells were kindly provided by Dr. Silvia Miotti (Istituto Nazionale per lo Studio e la Cura dei Tumori, Milan, Italy). Special FFRPMI cell culture medium (without folic acid, vitamin $B_{12}$, phenol red) was purchased from Cell Culture Technologies GmbH, Gravesano/Lugano, Switzerland. HPLC analyses were performed on a Merck-Hitachi L-6200A-system equipped with an L-3000 tunable absorption detector, a Berthold LB 508 radiometric detector and an XTerra® (Waters) MS C-18 reversed phase column (5 µm, 15 cm×4.6 mm). HPLC solvents: Aqueous 0.05 M triethylammonium phosphate buffer, pH 7.0 (solvent A), methanol (solvent B). The HPLC system started with 100% A with a linear gradient to 20% A and 80% B over 15 min, followed by 5 min of 100% A with a flow rate of 1 mL/min. Radioactivity (γ-radiation of $^{99m}Tc$ and $^{188}Re$ respectively) was measured with a γ-counter (Cobra™ II, Model B 5003, Packard). In vivo imaging of the mice were preformed with a combined small-animal SPECT/CT-camera (X-SPECT™, Gamma Medica Inc.).

Cell Culture. KB cells (human nasopharyngeal carcinoma cell line) were cultured continuously in 150-$cm^2$ flask as monolayers at 37° C. in a humidified atmosphere containing 7.5% $CO_2$. The cells were folate-starved using a folate-deficient special FFRPMI 1640 medium (modified RPMI 1640 medium without folic acid, vitamin $B_{12}$ and phenol red), supplemented with 10% heat-inactivated fetal calf serum (FCS, as the only source of folate), L-glutamine and antibiotics (penicillin 100 IU/mL, streptomycin 100 µg/mL, fungizone 0.25 µg/mL). Cell culture media such as FCS-supplemented FRPMI are known to feature a final folate concentration of ~3 nM, i.e. a value at the low end of the physiological concentration in human serum (Antony et al, J. Biol. Chem. 1985; 260:4911-17).

Preparation of cells for in vitro experiments: Eighteen hours prior to each experiment, the cells were seeded in 12-well plates ($8\times10^5$ cells in 1 mL/well) with the corresponding solution of antifolate (MTX, RTX, PMX: 0, 0.2, 2.0, 20.0 µM; 1 mL/well) and incubated at 37° C. to form confluent monolayers over night. The experiments were performed in triplets for each concentration of antifolate (MTX, RTX and PMX respectively).

Preparation of cells for in vivo experiments: For subcutaneous inoculation of the mice sub-confluent cells were harvested by treatment with EDTA (1 mM) in PBS (1×, pH 7.4). The cells were then washed once with PBS and pelleted by spinning at 1000×g for 5 min at 20° C. The cells were resuspended in PBS to obtain a concentration of $50\times10^6$ cells/mL.

In Vitro Studies. The in vitro experiments were performed with cell monolayers, which were incubated at 37° C. over night. The supernatants with antifolates were removed from each well. The KB cell monolayers were rinsed twice with ice-cold PBS (pH 7.4). Pure FFRPMI medium (without FCS/L-glutamine/antibiotics, 97511) was added into each well. The well plates were pre-incubated at 37° C. for 10 min. A solution of the radiotracer 1a (25 µl, 1 MBq/mL) was added and the well plates were incubated again at 37° C. for 1 h. Then, the supernatants were removed and the monolayers washed with ice-cold buffer. Counted radioactivity in samples, washed only with PBS, could be ascribed to the total of FR-bound radiotracer on the cell surface and the internalized fraction. Cell samples, washed with stripping buffer (aqueous solution of 0.1 M acetic acid and 0.15 M NaCl, pH 3) in order to release radiotracers from FRs on the cell surface, enabled determination of the internalized fraction (Dixon et al, J. Biol. Chem. 1992; 267:24140-47; Ladino et al, Int. J. Cancer 1997; 73:859-64). The monolayers were lysed in 1N NaOH (1000 µL), transferred in 4 mL-tubes and homogenized by vortex and counted for radioactivity using a γ-counter.

In Vivo Studies. 4-5-week-old female, athymic nude mice (CD1-Foxn1/nu) were purchased from Charles River Laboratories (Sulzfeld, Germany). Mice were housed under conditions of controlled temperature (26° C.), humidity (68%) and daily light cycle (12 h light/12 h dark). The animals were fed with a folate-deficient rodent diet (to reduce their serum folate to a level near that of humans) (Mathias et al, J. Nucl. Med. 1996; 37:1003-08). After an acclimation period of 5-7 days, the mice were inoculated subcutaneously with the tumour cell suspension ($5 \times 10^6$ cells) into the subcutis of the axilla. Radiotracer distribution studies were performed 12-14 days after tumour cell inoculation. The radiotracer (100 µL, 1a: 3.5 MBq/mL or 1b: 7 MBq/mL) was administered via a lateral tail vein. Antifolates (MTX, RTX and PMX) were dosed according to literature experiments at the upper limit of the tolerated dose (Li et al, Clin. Exp. Pharmacol. Physiol. 2004; 31:267-70; Pritchard et al, Clin. Cancer Res. 2000; 6:4389-95; Hughes et al, Journal of Clinical Oncology 2002; 20:3533-44; Aherne et al, Br. J. Cancer 1998; 77:221-26). MTX was supplemented to the drinking water (80 mg/mL) or intravenously injected (400 µg), 24 h, 2 h, 1 h, 30 min and 15 min previous to the administration of radiotracer 1a. RTX (100 µg) and PMX (400 µg) respectively were administered intravenously 2 h, 1 h, 30 min and 15 min previous to the radiotracer 1a. The animals were sacrificed and dissected 4 h p.i. of the radiotracer 1a. Additional biodistribution experiments were performed (30 min), 1 h, 4 h and 24 h post injection of the radiotracer 1a or 1b respectively with (antifolate) pre-treated animals 1 h previous to the experiment. The selected tissues were removed, weighted, and counted for radioactivity to determine distribution of radioactivity within the test animal. The results were tabulated as percentage of the injected dose per gram (% ID/g) of weight tissue, using reference counts from a definite sample of the original injectate.

SPECT-Imaging Studies. Imaging experiments were performed with an X-SPECT™-system (Gamma Medica Inc.) with a single head SPECT device and CT-device, 24 h p.i. of the radiotracer 1a. The radiotracer (500 MBq) was administered via a lateral tail vein. The mice were anesthetized with an isoflurane/oxygene mixture and positioned in the SPECT-camera using the therefore intended animal bed. Depth of anesthesia was monitored by measuring respiratory frequency. Body temperature was controlled by a rectal probe and kept at 37° C. by a thermocoupler and a heated air stream. SPECT data were acquired and reconstructed by software LumaGEM (version 5.407 µm 10). CT data were acquired by X-Ray CT-system (Gamma Medica™) and reconstructed by software Cobra (version 4.5.1). Fusion of SPECT- and CT-data was performed by software IDL Virtual Machine™ (version 6.0). Images were generated by software Amira™ (version 3.1.1).

Scheme 1:
Preparation of Radiotracers 1a/b.

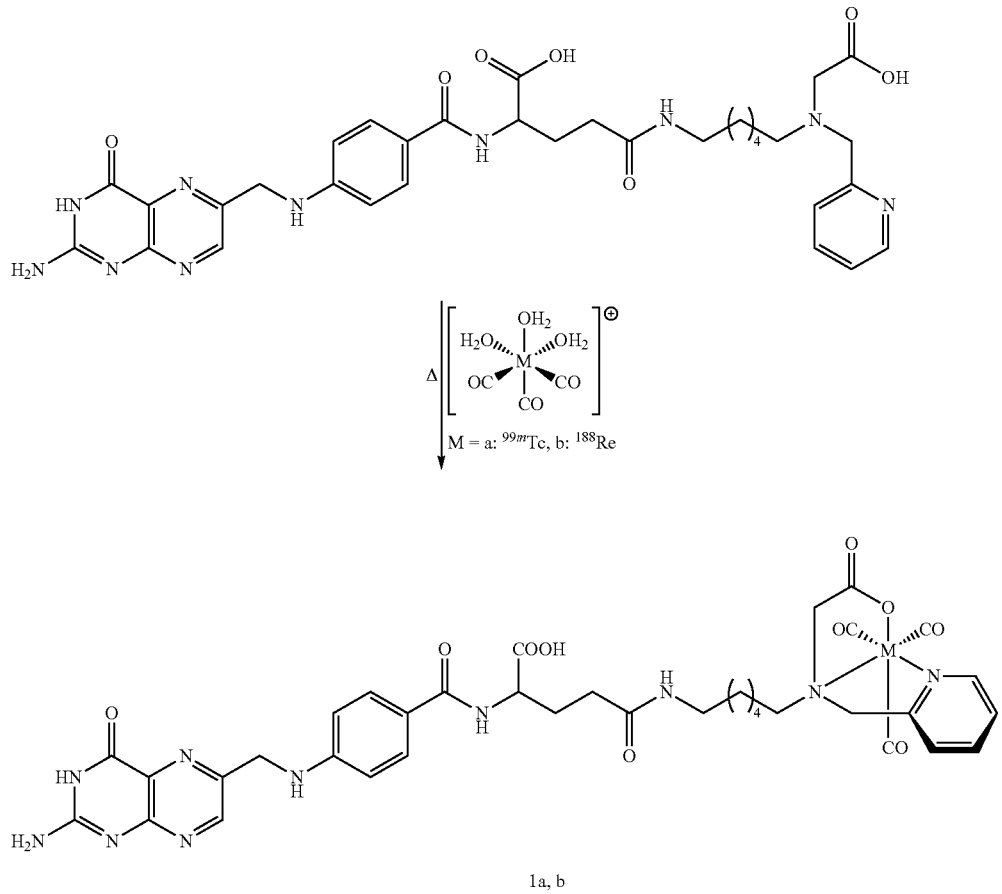

1a, b

The $^{99m}$Tc(CO)$_3$-folate radiotracer 1a was prepared according to the following procedure: The folate ligand (0.1 µmol, final concentration of 10$^{-4}$ M in the reaction vial) and the constituents of an Isolink™-kit (4.5 mg Na$_2$[H$_3$BCO$_2$], 2.9 mg B$_4$Na$_2$O$_7$, 7.8 mg Na$_2$CO$_3$, 9.0 mg NaKC$_4$H$_4$O$_6$.4H$_2$O) were placed in a sealed glass vial. 1 mL [Na][$^{99m}$TcO$_4$], eluted from the $^{99}$Mo/$^{99m}$Tc-generator, was added. After 45 min reaction time at 100° C. the vial was cooled on ice. The formation of the $^{99m}$Tc(CO)$_3$-complex 1a yielded in >95%. The radiolabeled complex 1a ($R_t$=15.5 min) was separated from unlabeled compound by means of HPLC ($R_t$=11.5 min) and diluted with phosphate buffered saline (PBS) to obtain a final concentration of 3.7 MBq/mL for in vivo biodistribution experiments or 3 GBq/mL for SPECT-imaging purposes respectively.

The fac-[$^{188}$Re(CO)$_3$(OH$_2$)$_3$]$^+$ precursor was prepared as previously reported with a slight modification (Schibli et al, Bioconjugate Chem. 2002; 13:750-56): A 7.5 mg amount of Na$_2$[H$_3$BCO$_2$] and 15 mg NH$_3$.BH$_3$ were placed in a 10 mL glass vial and flushed with argon. The $^{188}$Wo/$^{188}$Re-generator eluate (1 mL) was mixed with 20 mg concentrated H$_3$PO$_4$ (85%) prior to the injection in the reaction vial. The vial was incubated at 100° C. for 10 min to form the fac-[$^{188}$Re(CO)$_3$(OH$_2$)$_3$]$^+$ precursor in good yield (>90%). The final pH of the reaction solution was neutral. The $^{188}$Re(CO)$_3$-folate radiotracer 1b was prepared with fac-[$^{188}$Re(CO)$_3$(OH$_2$)$_3$]$^+$ (450 µl; ~1 GBq/mL) and a stock solution of the folate ligand in PBS (50 µL, 10$^{-2}$ M)), placed in a sealed glass vial and incubated for 60 min at 100° C. to form the radiotracer 1b (yield >85%). The radiolabeled compound 1b ($R_t$=15.5 min) was separated from unlabeled compound by means of HPLC ($R_t$=11.5 min) and diluted in PBS to obtain a final concentration of 7.4 MBq/mL for in vivo biodistribution experiments.

In Vitro Evaluation Using Antifolates.

In vitro experiments were performed in order to assess the influence of antifolates on cell accumulation of the radiotracer 1a. KB cells were incubated with various concentrations of anti-folates (MTX, RTX, and PMX) previous to the cell binding experiments. In samples, incubated for 20 h with the highest concentration of antifolates (10 µM), we found 65-80% of total added radioactivity specifically cell associated compared to only 25-35% in untreated controls (Table 1). The acid-resistant fraction of radioactivity, which could be ascribed to internalized radiotracers, revealed also increased (19-27% vs. control: 5-10%) in antifolate pre-treated cells (Table 1).

TABLE 1

In vitro cell binding and internalization of radiotracer 1a, using KB-cells, pre-treated with antifolates

| | Methotrexate | | Raltitrexed | | Pemetrexed | |
|---|---|---|---|---|---|---|
| | total binding (%) | Internalization (%) | total binding (%) | Internalization (%) | total binding (%) | Internalization (%) |
| 0.0 µM | 31.8 ± 7.0 | 4.5 ± 0.9 | 25.7 ± 0.6 | 7.8 ± 0.5 | 34.6 ± 1.4 | 10.2 ± 1.2 |
| 0.1 µM | 42.1 ± 12.8 | 10.8 ± 0.1 | 35.3 ± 3.6 | 12.1 ± 1.0 | 55.1 ± 9.8 | 17.6 ± 1.6 |
| 1.0 µM | 68.0 ± 8.7 | 13.1 ± 1.3 | 48.5 ± 8.0 | 14.0 ± 1.9 | 66.9 ± 2.3 | 15.7 ± 1.0 |
| 10 µM | 77.3 ± 5.7 | 18.8 ± 1.8 | 64.5 ± 3.5 | 19.0 ± 2.2 | 78.8 ± 10.7 | 26.7 ± 4.7 |

Figure 3:
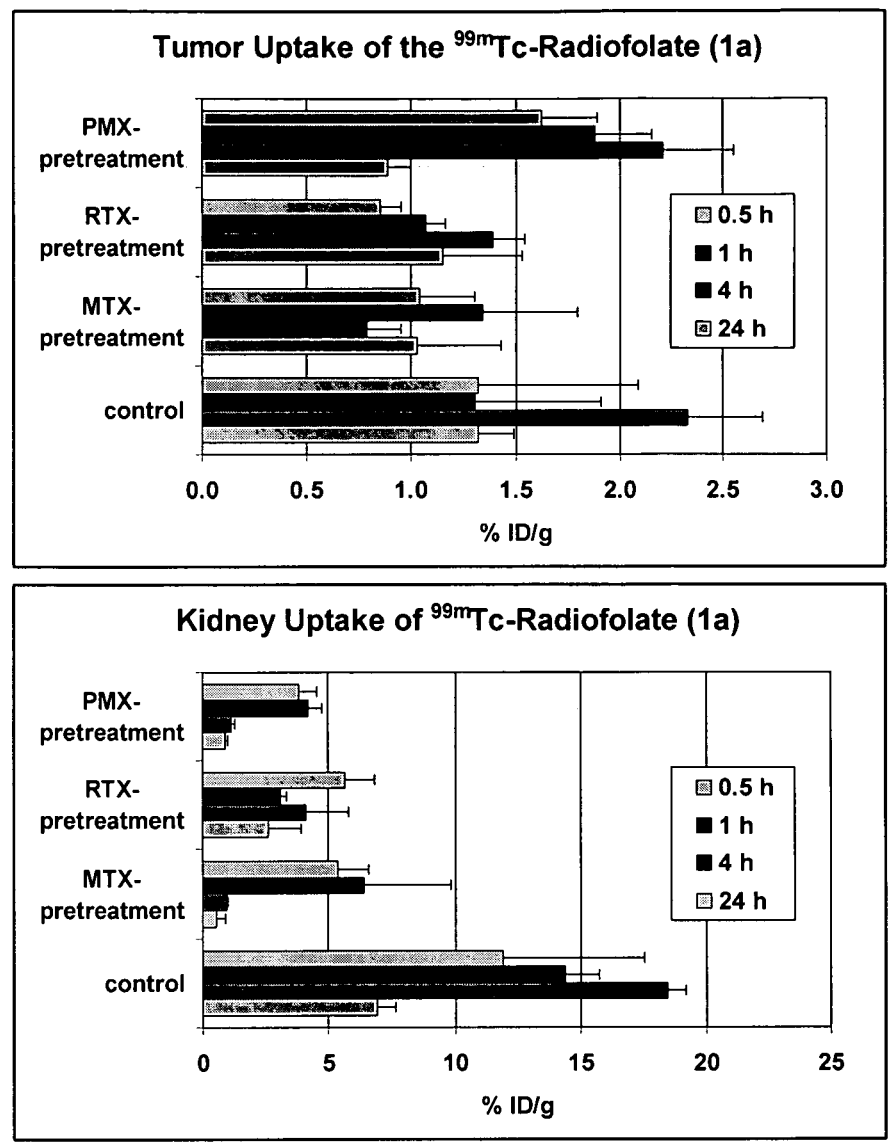
FIG. 3. Time-dependent uptake of radiotracer 1a in tumour and kidney of mice, pre-treated with antifolates (MTX, RTX, and PMX), 1 h previous to the administration of 1a, compared to control mice.
Figure 7:
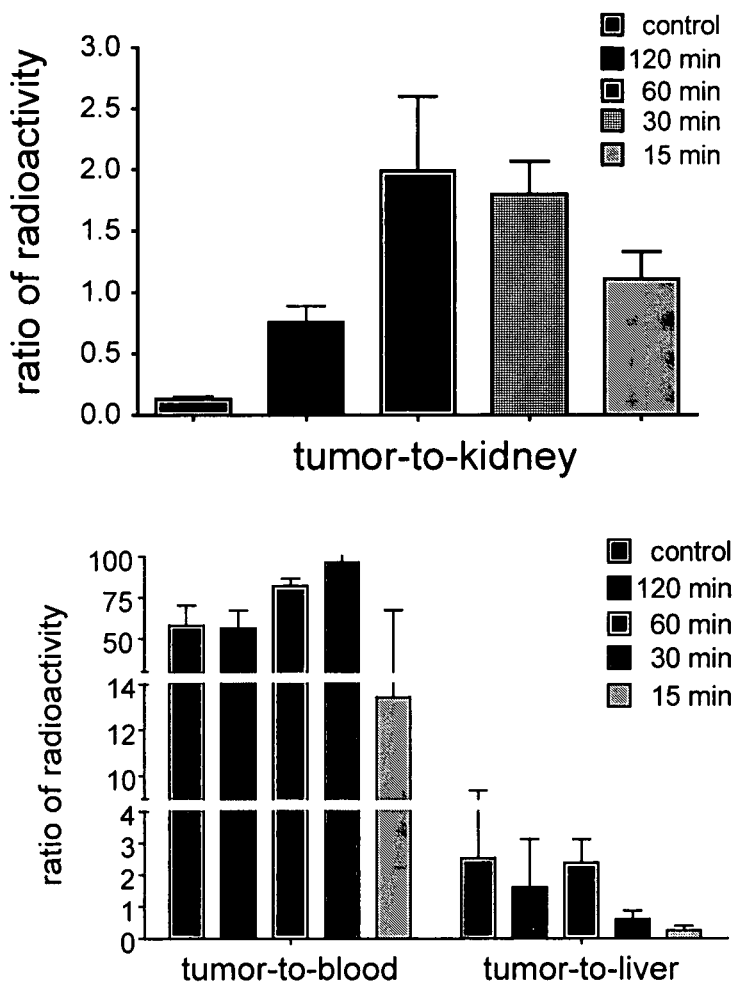
FIG. 7. Tumor-to-non-tumor ratios of the radiotracer 1a (4 h p.i.) for selected organs and tissue depending on the time point of PMX pre-injection.

Detailed in vivo studies were performed in order to investigate the influence of antifolates, injected at short time points (2 h, 1 h, 30 min or 15 min) previous to the administration of the radiotracer 1a (FIGS. 3 and 7). Apart from MTX we also challenged antifolates of the new generation, RTX and PMX. For all three antifolates the same general phenomenon could be observed: (i) Significantly reduced renal accumulation of radioactivity, while (ii) almost retained uptake in the tumour and (iii) optimal tumour-to-background ratios of radioactivity in mice, pre-treated with antifolates 1 h previous to the radiotracer (Table 2; FIG. 3; data of RTX not shown).

In Vivo Evaluation of $^{99m}$Tc(CO)$_3$-Folate (1a) in Combination with MTX, RTX and PMX Respectively:

TABLE 2

Biodistribution data of folate radiotracer 1a, 4 h p.i. with antifolate (MTX, RTX or PMX) pre-injection at different points in time, previous to the radiotracer administration or post administration.

| | 2 h$^a$ | 1 h$^a$ | 30 min$^a$ | 15 min$^a$ | Post 1 h$^b$ |
|---|---|---|---|---|---|
| | Methotrexate | | | | |
| blood | 0.02 ± 0.00 | 0.01 ± 0.01 | 0.01 ± 0.00 | 0.09 ± 0.08 | 0.01 ± 0.06 |
| heart | 0.04 ± 0.01 | 0.02 ± 0.01 | 0.01 ± 0.00 | 0.06 ± 0.09 | 0.72 ± 0.74 |
| lung | 0.05 ± 0.01 | 0.04 ± 0.01 | 0.08 ± 0.11 | 0.14 ± 0.14 | 1.66 ± 1.78 |
| spleen | 0.03 ± 0.01 | 0.04 ± 0.04 | 0.05 ± 0.07 | 0.07 ± 0.02 | 0.28 ± 0.25 |
| kidney | 5.15 ± 0.38 | 2.45 ± 1.32 | 1.03 ± 0.20 | 0.73 ± 0.24 | 5.56 ± 2.64 |
| stomach | 0.37 ± 0.29 | 0.09 ± 0.04 | 0.19 ± 0.06 | 0.40 ± 0.28 | 0.44 ± 0.31 |
| intestines | 1.78 ± 0.43 | 0.90 ± 0.71 | 0.52 ± 0.14 | 0.54 ± 0.23 | 1.66 ± 0.38 |
| contents of intestines | 7.79 ± 1.22 | 9.37 ± 10.27 | 4.14 ± 1.65 | 4.16 ± 3.55 | 24.18 ± 13.23 |
| liver | 3.71 ± 3.12 | 0.85 ± 0.79 | 1.07 ± 1.23 | 0.35 ± 0.09 | 3.25 ± 2.52 |

TABLE 2-continued

Biodistribution data of folate radiotracer 1a, 4 h p.i. with antifolate (MTX, RTX or PMX) pre-injection at different points in time, previous to the radiotracer administration or post administration.

|  | 2 h[a] | 1 h[a] | 30 min[a] | 15 min[a] | Post 1 h[b] |
|---|---|---|---|---|---|
| muscle | 0.09 ± 0.03 | 0.06 ± 0.02 | 0.03 ± 0.01 | 0.03 ± 0.01 | 0.15 ± 0.11 |
| bone | 0.06 ± 0.04 | 0.02 ± 0.01 | 0.01 ± 0.00 | 0.03 ± 0.01 | 0.13 ± 0.07 |
| tumour | 0.91 ± 0.25 | 1.41 ± 0.65 | 0.63 ± 0.02 | 0.58 ± 0.12 | 2.45 ± 0.28 |
| tumour-to-blood | 42.43 ± 8.04 | 133.9 ± 46.8 | 57.16 ± 7.37 | 23.58 ± 32.11 | 94.59 ± xx |
| tumour-to-liver | 0.87 ± 1.24 | 2.61 ± 1.81 | 1.30 ± 1.04 | 1.83 ± 0.92 | 1.90 ± 2.16 |
| tumour-to-kidney | 0.18 ± 0.04 | 0.59 ± 0.12 | 0.62 ± 0.14 | 0.87 ± 0.38 | 0.49 ± 0.23 |
| Raltitrexed | | | | | |
| blood | 0.02 ± 0.01 | 0.01 ± 0.00 | 0.04 ± 0.05 | 0.01 ± 0.00 | |
| heart | 0.07 ± 0.02 | 0.03 ± 0.01 | 0.04 ± 0.01 | 0.03 ± 0.01 | |
| lung | 0.10 ± 0.02 | 0.04 ± 0.01 | 0.07 ± 0.02 | 0.04 ± 0.02 | |

More detailed biodistribution studies with the $^{99m}$Tc(CO)$_3$— radiotracer 1a were performed 30 min, 1 h, 4 h and 24 h post injection, after pre-treatment of the mice with anti-folates, 1 h previous to the radiotracer (Table 3). The tumour uptake was highest 4 h p.i. of the radiotracer 1a in RTX- and PMX pre-treated mice and 1 h p.i. in MTX pre-treated mice. Tumour-to-kidney ratios gradually increased up to 2.33±1.03 (24 h p.i.) in MTX pre-treated mice and similar data were found in RTX-pre-treated mice, whereas PMX pre-treatment resulted in a maximal tumour-to-kidney ratio 4 h p.i. of the radiotracer 1a (1.88±0.51), decreasing to 0.80±0.08 after 24 h. The same time course could be observed of maximal tumour-to-blood and tumour-to-liver ratios of radioactivity.

TABLE 3

Influence of MTX[a], RTX[a] and PMX[a] respectively on the biodistribution data of radiotracer 1a in athymic nude mice, bearing KB-cell xenografts

|  | 30 min p.i. | 1 h p.i. | 4 h p.i. | 24 h p.i. |
|---|---|---|---|---|
| Methotrexate[a] | | | | |
| blood | 0.14 ± 0.01 | 0.06 ± 0.02 | 0.02 ± 0.00 | 0.00 ± 0.00 |
| heart | 0.15 ± 0.03 | 0.09 ± 0.05 | 0.02 ± 0.01 | 0.03 ± 0.01 |
| lung | 0.21 ± 0.05 | 0.11 ± 0.05 | 0.02 ± 0.01 | 0.02 ± 0.00 |
| spleen | 0.06 ± 0.01 | 0.15 ± 0.23 | 0.01 ± 0.01 | 0.01 ± 0.00 |
| kidney | 5.37 ± 1.19 | 6.36 ± 3.44 | 0.95 ± 0.07 | 0.54 ± 0.40 |
| stomach | 2.18 ± 2.52 | 1.41 ± 1.10 | 0.46 ± 0.27 | 2.88 ± 3.82 |
| intestines | 38.75 ± 25.77 | 8.12 ± 5.25 | 2.19 ± 1.57 | 0.10 ± 0.08 |
| contents of intestines | 109.20 ± 68.16 | 80.71 ± 75.28 | 17.15 ± 13.44 | 0.19 ± 0.50 |
| liver | 7.20 ± 2.36 | 6.09 ± 3.81 | 5.05 ± 5.30 | 0.23 ± 0.02 |
| muscle | 0.25 ± 0.10 | 0.21 ± 0.10 | 0.11 ± 0.10 | 0.02 ± 0.02 |
| bone | 0.13 ± 0.04 | 0.19 ± 0.14 | 0.01 ± 0.01 | 0.02 ± 0.02 |
| tumour | 1.04 ± 0.26 | 1.34 ± 0.46 | 0.79 ± 0.16 | 1.03 ± 0.40 |
| tumour-to-blood | 7.31 ± 1.69 | 24.31 ± 5.96 | 51.39 ± 17.42 | 136.8 ± 32.0 |
| tumour-to-liver | 0.15 ± 0.03 | 0.25 ± 0.08 | 0.57 ± 0.76 | 4.52 ± 1.50 |
| tumour-to-kidney | 0.19 ± 0.01 | 0.23 ± 0.08 | 0.83 ± 0.11 | 2.33 ± 1.03 |
| Raltitrexed[a] | | | | |
| blood | 1.59 ± 2.55 | 0.01 ± 0.00 | 0.04 ± 0.05 | 0.01 ± 0.00 |
| heart | 0.23 ± 0.22 | 0.03 ± 0.01 | 0.04 ± 0.01 | 0.03 ± 0.01 |
| lung | 0.50 ± 0.45 | 0.04 ± 0.01 | 0.07 ± 0.02 | 0.04 ± 0.02 |
| spleen | 0.20 ± 0.13 | 0.03 ± 0.01 | 0.04 ± 0.01 | 0.04 ± 0.02 |
| kidney | 5.66 ± 1.16 | 3.08 ± 0.28 | 4.10 ± 1.71 | 2.63 ± 1.29 |
| stomach | 0.55 ± 0.10 | 0.06 ± 0.03 | 0.40 ± 0.42 | 0.11 ± 0.06 |
| intestines | 8.24 ± 3.08 | 1.13 ± 1.27 | 1.01 ± 0.28 | 0.63 ± 0.28 |
| contents of intestines | 44.57 ± 78.83 | 14.58 ± 17.85 | 10.28 ± 3.36 | 8.56 ± 9.04 |
| liver | 6.86 ± 5.58 | 0.47 ± 0.36 | 2.70 ± 2.14 | 1.53 ± 0.37 |
| muscle | 0.19 ± 0.08 | 0.04 ± 0.03 | 0.07 ± 0.03 | 0.05 ± 0.02 |
| bone | 0.11 ± 0.04 | 0.01 ± 0.01 | 0.03 ± 0.01 | 0.01 ± 0.02 |
| tumour | 0.85 ± 0.10 | 1.07 ± 0.09 | 1.39 ± 0.15 | 1.15 ± 0.38 |
| tumour-to-blood | 6.32 ± 7.10 | 84.52 ± 28.27 | 66.88 ± 54.12 | 120.77 ± 43.10 |
| tumour-to-liver | 0.19 ± 0.13 | 4.88 ± 5.52 | 0.89 ± 0.81 | 0.74 ± 0.07 |
| tumour-to-kidney | 0.15 ± 0.03 | 0.35 ± 0.05 | 0.38 ± 0.15 | 0.47 ± 0.12 |
| Pemetrexed[a] | | | | |
| blood | 0.09 ± 0.04 | 0.28 ± 0.02 | 0.02 ± 0.01 | 0.02 ± 0.00 |
| heart | 0.54 ± 0.09 | 0.48 ± 0.03 | 0.09 ± 0.07 | 0.05 ± 0.04 |
| lung | 0.38 ± 0.08 | 0.56 ± 0.06 | 0.19 ± 0.08 | 0.08 ± 0.00 |
| spleen | 0.11 ± 0.04 | 0.23 ± 0.14 | 0.39 ± 0.55 | 0.03 ± 0.01 |
| kidney | 3.84 ± 0.72 | 4.19 ± 0.53 | 1.14 ± 0.18 | 0.90 ± 0.10 |
| stomach | 1.38 ± 1.36 | 1.19 ± 0.55 | 5.85 ± 9.27 | 0.53 ± 0.19 |

TABLE 3-continued

Influence of MTX[a], RTX[a] and PMX[a] respectively on the biodistribution data of radiotracer 1a in athymic nude mice, bearing KB-cell xenografts

|  | 30 min p.i. | 1 h p.i. | 4 h p.i. | 24 h p.i. |
|---|---|---|---|---|
| intestines | 17.77 ± 14.60 | 3.99 ± 5.47 | 1.34 ± 0.20 | 0.15 ± 0.04 |
| contents of intestines | 214.5 ± 188.6 | 50.46 ± 29.90 | 21.31 ± 18.25 | 1.34 ± 1.32 |
| liver | 6.87 ± 2.82 | 17.78 ± 3.64 | 0.97 ± 0.25 | 1.10 ± 0.04 |
| muscle | 0.56 ± 0.15 | 0.61 ± 0.07 | 0.97 ± 0.25 | 0.11 ± 0.02 |
| bone | 0.28 ± 0.15 | 0.35 ± 0.05 | 0.22 ± 0.04 | 0.06 ± 0.04 |
| tumour | 1.62 ± 0.27 | 1.88 ± 0.28 | 2.21 ± 0.34 | 0.89 ± 0.11 |
| tumour-to-blood | 20.52 ± 5.66 | 6.84 ± 1.47 | 82.07 ± 4.39 | 38.97 ± 2.57 |
| tumour-to-liver | 0.43 ± 0.07 | 0.11 ± 0.02 | 2.38 ± 0.73 | 0.80 ± 0.08 |
| tumour-to-kidney | 0.25 ± 0.07 | 0.45 ± 0.01 | 1.99 ± 0.51 | 0.99 ± 0.03 |

[a]pre-injected 1 h previous to the radiotracer

In Vivo Evaluation of $^{188}$Re(CO)$_3$-Folate in Combination with PMX.

Biodistribution of the $^{188}$Re(CO)$_3$-folate radiotracer 1b was assessed in mice, pre-treated with PMX, 1 h previous to the injection of the radiotracer (Table 6). Tumour uptake of radiotracer 1b was slightly reduced in pre-treated mice (1.16±0.16% ID/g, 4 h p.i.) compared to control mice (1.87±0.04% ID/g, 4 h p.i.). However, tumour-to-kidney ratio was also significantly improved (1.59±0.30, 4 h p.i.), relative to untreated mice (0.16±0.01, 4 h p.i.) as found with radiotracer 1a. The tumour uptake of radiotracer 1b (1.16±0.16% ID/g, 4 h p.i.) was lower than the tumour uptake of radiotracer 1a (2.21±0.34% ID/g, 4 h p.i.) in PMX pre-treated mice. Favourable tumour-to-kidney ratios were similar for both of the radiotracers (1b: 1.59±0.30 vs. 1a: 1.99±0.51) and significantly superior to those, observed in control mice (1b: 0.16±0.01 vs. 1a: 0.13±0.02; 4 h p.i.).

TABLE 4

Biodistribution data of radiotracer 1b in athymic nude mice, bearing KB-cell xenografts, with PMX[a] pre-treatment.

|  | Pemetrexed[a] | | |
|---|---|---|---|
|  | 1 h p.i. | 4 h p.i. | 24 h p.i. |
| blood | 0.99 ± 1.41 | 0.07 ± 0.06 | 0.03 ± 0.00 |
| heart | 1.07 ± 1.24 | 0.13 ± 0.03 | 0.04 ± 0.01 |
| lung | 0.47 ± 0.34 | 0.14 ± 0.01 | 0.05 ± 0.00 |
| spleen | 0.29 ± 0.31 | 0.05 ± 0.00 | 0.02 ± 0.00 |
| kidney | 1.99 ± 0.31 | 0.74 ± 0.13 | 0.58 ± 0.12 |
| stomach | 1.30 ± 0.28 | 0.83 ± 0.36 | 0.85 ± 1.44 |
| intestines | 2.80 ± 1.05 | 0.76 ± 0.55 | 0.11 ± 0.11 |
| contents of intestines | 26.66 ± 9.67 | 6.08 ± 2.83 | 0.78 ± 1.12 |
| liver | 4.21 ± 0.88 | 2.03 ± 1.50 | 0.18 ± 0.03 |
| muscle | 0.41 ± 0.19 | 0.15 ± 0.03 | 0.05 ± 0.02 |
| bone | 0.39 ± 0.19 | 0.10 ± 0.02 | 0.01 ± 0.01 |
| tumour | 1.30 ± 0.15 | 1.16 ± 0.16 | 0.88 ± 0.23 |
| tumour-to-blood | 5.01 ± 3.93 | 10.57 ± 2.07 | 30.25 ± 8.76 |

TABLE 4-continued

Biodistribution data of radiotracer 1b in athymic nude mice, bearing KB-cell xenografts, with PMX[a] pre-treatment.

|  | Pemetrexed[a] | | |
|---|---|---|---|
|  | 1 h p.i. | 4 h p.i. | 24 h p.i. |
| tumour-to-liver | 0.32 ± 0.10 | 1.01 ± 0.96 | 5.03 ± 1.12 |
| tumour-to-kidney | 0.66 ± 0.03 | 1.59 ± 0.30 | 1.57 ± 0.52 |

[a]pre-injected 1 h previous to the radiotracer

SPECT/CT-studies. Combined SPECT/CT-studies were preformed with untreated mice as well as with PMX-pre-treated mice using a dedicated small animal scanner. Distribution of radioactivity in a living mouse, 24 h p.i. of the radiotracer 1a, is shown in FIG. 4A (without preinjection) and FIG. 4B (with preinjection. The radiotracer predominantly accumulated in FR-positive tissues (tumours and kidneys).

Figure 4:
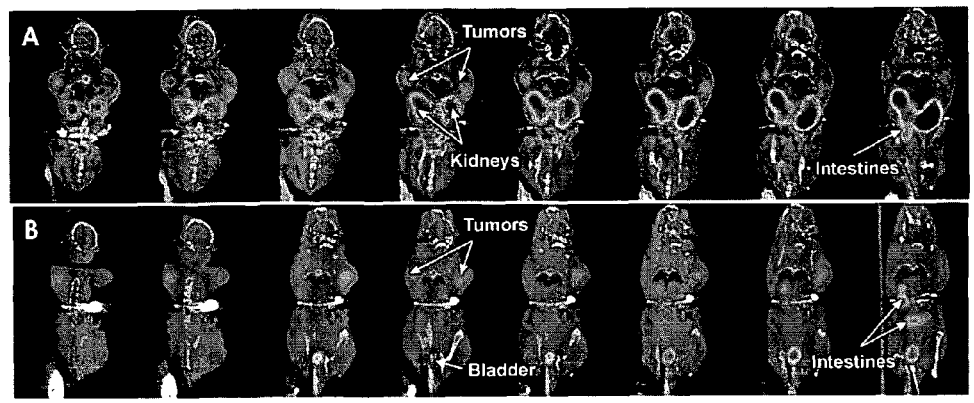
FIG. 4. Selected sections of combined SPECT (colour)/CT (black/white) (high sensitivity, low resolution parallel collimator) of living mice, bearing KB-cell tumours, 24 h p.i. of the radiotracer 1a. (A) Without and (B) with PMX pre-injection.
Figure 5:
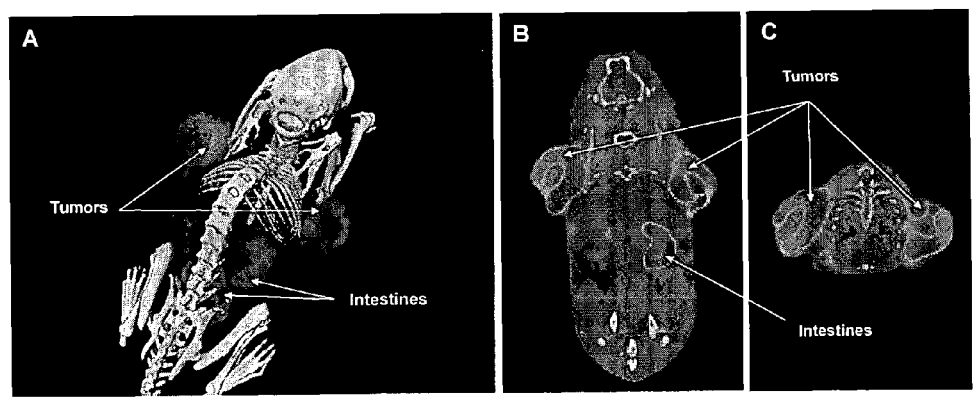
FIG. 5. Whole body SPECT/CT (high resolution, low sensitivity, pinhole collimator) of a PMX pre-injected mouse, bearing KB-cell tumours on the left and right shoulders, 24 h p.i. of the radiotracer: (A) 3-dimensional picture, (B) frontal section and (C) transversal section.
Figure 6:
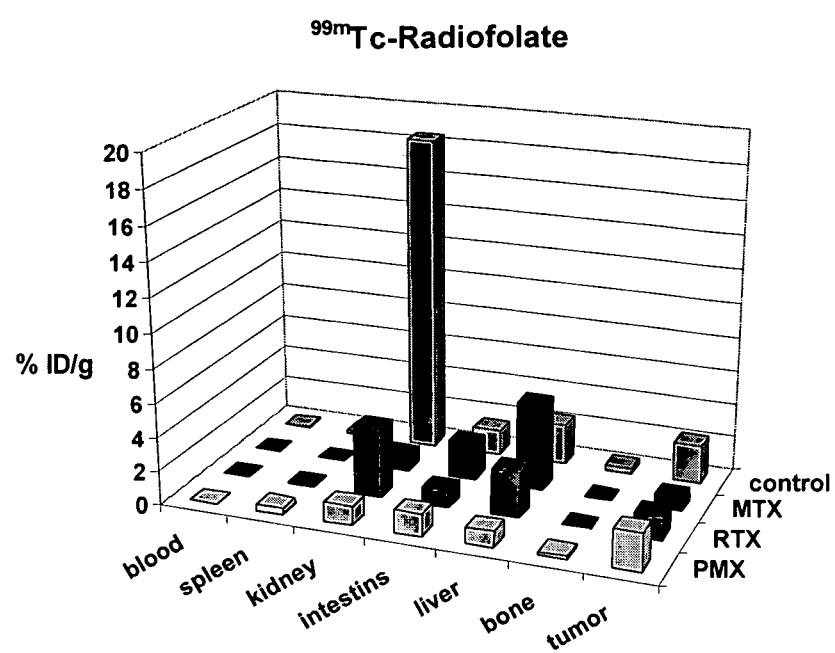
FIG. 6. Biodistribution 4 h p.i. of radiotracer 1a of control mice or mice, pre-treated with antifolates (MTX, RTX, PMX), 1 h previous to the administration of 1a/b.

Distribution of radioactivity in a mouse, pre-treated with PMX 1 h previous to the radiotracer 1a, is shown in FIG. 4A (without preinjection). These pictures clearly confirmed data from the ex-vivo biodistribution studies (Table 3). In the pre-treated mouse radioactivity is still accumulated in tumours, but kidneys are almost completely blocked and only unspecifically distributed radioactivity was detectable in the gastrointestinal tract (FIG. 4). The pre-treated mouse was also scanned post-mortem with a high resolution pinhole collimator (FIG. 5).

Example 2

In Vivo Evaluation of Different Folate Radiotracers (2a, 3a) in Combination with MTX and PMX Respectively The effect of antifolates with respect to selective protection of kidney tissue is not limited to compound 1a/b but is applicable to structurally different complexes as mentioned above including e.g. complexes 2a and 3a. Biodistribution of the radiotracers 2a and 3a were assessed in mice, with or without pre-treated with PMX or MTX respectively, 1 h previous to the injection of the radiotracer (Table 5).

TABLE 5

Biodistribution 4 h p.i. data of radiotracer 2a and 3a in athymic nude mice, bearing KB xenografts with or without PMX or MTX pre-treatment.

| Organs | 2a | 2a + PMX[a] | 3a | 3a + MTX[a] |
|---|---|---|---|---|
| blood | 0.19 ± 0.18 | 0.07 ± 0.02 | 0.03 ± 0.01 | 0.01 ± 0.00 |
| heart | 0.80 ± 0.60 | 0.72 ± 0.39 | 0.20 ± 0.09 | 0.02 ± 0.00 |
| lung | 0.85 ± 0.08 | 0.50 ± 0.19 | 0.20 ± 0.02 | 0.02 ± 0.00 |
| spleen | 0.30 ± 0.05 | 0.19 ± 0.03 | 0.08 ± 0.02 | 0.01 ± 0.00 |
| kidney | 42.02 ± 7.31 | 5.05 ± 0.67 | 7.11 ± 0.75 | 0.78 ± 0.17 |
| stomach | 0.62 ± 0.22 | 0.46 ± 0.22 | 0.54 ± 0.58 | 0.14 ± 0.06 |

TABLE 5-continued

Biodistribution 4 h p.i. data of radiotracer 2a and 3a in athymic nude mice, bearing KB xenografts with or without PMX or MTX pre-treatment.

| Organs | 2a | 2a + PMX[a] | 3a | 3a + MTX[a] |
|---|---|---|---|---|
| intestines | 0.79 ± 0.43 | 1.41 ± 1.21 | 0.71 ± 0.40 | 1.99 ± 3.13 |
| contents of intest. | 7.72 ± 4.36 | 12.43 ± 15.01 | 2.49 ± 12.10 | 39.36 ± 65.95 |
| liver | 4.51 ± 1.29 | 1.91 ± 1.38 | 1.72 ± 2.04 | 1.29 ± 0.77 |
| muscle | 1.31 ± 0.28 | 0.95 ± 0.26 | 0.27 ± 0.01 | 0.02 ± 0.01 |
| bone | 0.82 ± 0.13 | 0.56 ± 0.25 | 0.16 ± 0.02 | 0.01 ± 0.01 |
| tumour | 3.72 ± 0.89 | 3.89 ± 0.42 | 0.82 ± 0.27 | 0.30 ± 0.08 |
| tumour-to-blood | 12.29 ± 4.22 | 54.25 ± 14.10 | 27.00 ± 14.60 | 23.93 ± 2.98 |
| tumour-to-liver | 0.88 ± 0.38 | 2.86 ± 1.76 | 1.24 ± 1.03 | 0.30 ± 0.18 |
| tumour-to-kidney | 0.09 ± 0.02 | 0.77 ± 0.04 | 0.12 ± 0.05 | 0.41 ± 0.19 |

[a]pre-injected 1 h previous to the radiotracer

Example 3

In Vivo Evaluation of $^{99m}Tc(CO)_3$-Folate (1a) in Combination with MTX Using Different Folate Receptor Positive Tumour Cell Xenografts The effect of antifolates with respect to selective protection of kidney tissue is not limited to KB cancer cells but to all cell lines expressing the folate receptor and activated (but not resting) synovial macrophages.

4-5-week-old female, athymic nude mice (CD1-Foxn1/nu) were purchased from Charles River Laboratories (Sulzfeld, Germany). Mice were housed under conditions of controlled temperature (26° C.), humidity (68%) and daily light cycle (12 h light/12 h dark). The animals were fed with a folate-deficient rodent diet (to reduce their serum folate to a level near that of humans) (Mathias et al, J. Nucl. Med. 1996; 37:1003-08). After an acclimation period of 5-7 days, the mice were inoculated subcutaneously with the tumour cell suspension using IGROV-1 and KB-V1 (multiresistant) cells ($5 \times 10^6$ cells) into the subcutis of the axilla. Radiotracer distribution studies were performed 12-14 days after tumour cell inoculation (Table 6). The radiotracer (100 µL, 1a: 3.5 MBq/mL or 1b: 7 MBq/mL) was administered via a lateral tail vein. MTX, was dosed according to literature experiments at the upper limit of the tolerated dose (Li et al, Clin. Exp. Pharmacol. Physiol. 2004; 31:267-70; Pritchard et al, Clin. Cancer Res. 2000; 6:4389-95; Hughes et al, Journal of Clinical Oncology 2002; 20:3533-44; Aherne et al, Br. J. Cancer 1998; 77:221-26).

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and, all parts and percentages are by weight, unless otherwise indicated.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

The invention claimed is:

1. A method for selective targeting of one or more effector moieties to diseased cells in a mammal, said diseased cells expressing or overexpressing a folate receptor, as compared to normal kidney cells expressing a folate receptor, comprising simultaneous or sequential administration of effective amounts of an antifolate, and a folate- or pteroate-conjugate comprising said one or more effector moieties, wherein
the folate or pteroate is selected from the group consisting of folic acid, pteroic acid, folinic acid, pteropoly-

TABLE 6

Biodistribution data of radiotracer 1a in athymic nude mice, bearing IGROV-1 and KB-V1 (multiresistant) xenografts

| Tumour Cells | IGROV-1 | IGROV-1[a] | KB-V1 | KB-V1[a] |
|---|---|---|---|---|
| blood | 0.05 ± 0.01 | 0.01 ± 0.00 | 0.09 ± 0.09 | 0.03 ± 0.00 |
| heart | 0.67 ± 0.41 | 0.01 ± 0.00 | 0.25 ± 0.06 | 0.03 ± 0.00 |
| lung | 0.28 ± 0.04 | 0.01 ± 0.00 | 0.25 ± 0.03 | 0.03 ± 0.00 |
| spleen | 0.13 ± 0.03 | 0.01 ± 0.01 | 0.09 ± 0.03 | 0.01 ± 0.00 |
| kidney | 15.80 ± 1.13 | 1.12 ± 0.33 | 12.05 ± 0.98 | 0.68 ± 0.12 |
| stomach | 0.51 ± 0.17 | 0.55 ± 0.73 | 0.14 ± 0.06 | 0.14 ± 0.12 |
| intestines | 0.88 ± 0.40 | 1.78 ± 1.64 | 0.56 ± 0.21 | 0.21 ± 0.07 |
| contents of intest. | 4.04 ± 4.17 | 17.16 ± 19.72 | 3.87 ± 0.49 | 1.64 ± 0.59 |
| liver | 2.14 ± 1.05 | 2.80 ± 1.84 | 0.44 ± 0.28 | 1.97 ± 1.23 |
| muscle | 0.39 ± 0.08 | 0.03 ± 0.02 | 0.27 ± 0.05 | 0.03 ± 0.01 |
| bone | 0.23 ± 0.06 | 0.01 ± 0.01 | 0.15 ± 0.04 | 0.02 ± 0.01 |
| tumour | 1.44 ± 0.14 | 0.43 ± 0.06 | 1.33 ± 0.26 | 0.48 ± 0.03 |
| tumour-to-blood | 29.42 ± 8.40 | 63.84 ± 13.26 | 22.41 ± 12.47 | 18.26 ± 0.75 |
| tumour-to-liver | 0.76 ± 0.25 | 0.20 ± 0.13 | 4.40 ± 3.82 | 0.39 ± 0.36 |
| tumour-to-kidney | 0.09 ± 0.01 | 0.40 ± 0.14 | 0.11 ± 0.03 | 0.72 ± 0.09 |

[a]pre-injected of MXT 1 h previous to the radiotracer glutamic acid, and folate receptor-binding pteridines selected from the group consisting of tetrahydropterins, dihydrofolates, tetrahydrofolates, and deaza and dideaza analogs thereof, or salt, ester or polyglutamated form thereof;

the amount of antifolate administered is effective to selectively target the folate- or pteroate-conjugate comprising one or more effector moieties to diseased cells as compared to normal kidney cells;

the effector moieties comprise a diagnostic or therapeutic agent;

the amount of folate- or pteroate-conjugate comprising one or more effector moieties is diagnostically or therapeutically effective; and simultaneous or sequential administration of the antifolate and the folate- or pteroate-conjugate is effective to selectively target the effector moiety to diseased cells expressing or overexpressing a folate receptor relative to normal kidney cells expressing a folate receptor, as compared to administration of the conjugate in the absence of an effective amount of the antifolate, wherein sequential administration occurs within 24 hours.

2. The method of claim 1, comprising:
   i) administering an effective amount of an antifolate, followed by
   ii) administering an effective amount of a folate- or pteroate-conjugate comprising said one or more effector moieties.

3. The method of claim 1, comprising:
   i) administering an effective amount of a folate- or pteroate-conjugate comprising said one or more effector moieties, followed by
   ii) administering an effective amount of an antifolate.

4. The method of claim 1, wherein said diseased cells are tumour cells or activated macrophages.

5. The method of claim 1, wherein said folate- or pteroate-conjugate comprises a folate or pteroate through a spacer to said one or more effector moieties.

6. The method of claim 5, wherein said folate or pteroate is selected from the group consisting of folic acid, pteroic acid, folinic acid, pteropolyglutamic acid, folate receptor-binding pteridines, tetrahydropterins, dihydrofolates, tetrahydrofolates, 5-substituted derivatives selected from 5-formyltetrahydrofolic acid or 5-methyltetrahydrofolic acid, 10-substituted derivative 10-formyltetrahydrofolic acid, 5,10 substituted or 5,10-bridged derivatives selected from 5,10-methylenetetrahydrofolic acid or 5,10-methenyltetrahydrofolic acid; their deaza and dideaza analogs and salts, esters and polyglutamated forms thereof.

7. The method of claim 4, wherein said folate or pteroate is 5-formyltetrahydrofolic acid, 5-methyltetrahydrofolic acid, 10-formyltetrahydrofolic acid, 5,10-methylenetetrahydrofolic acid or 5,10-methenyltetrahydrofolic acid, or salt, ester or polyglutamated form thereof.

8. The method of claim 1, wherein said antifolate is an inhibitor of a folate-dependent enzyme.

9. The method of claim 1, wherein said therapeutic agent comprises a pharmacologically active agent compound selected from the group consisting of peptides, oligopeptides, proteins, glycoproteins, antigens and antibodies thereto, amino acids, nucleotides, oligonucleotides, polynucleotides, lipids, phospholipids; toxins; antibiotics; antiviral agents; antimicrobial agents; H-2 antagonists; chemotherapeutics; antisense therapeutics; gene therapeutics; antibody therapeutics; anti-cytokine therapeutics; and antimetabolite therapeutics.

10. The method of claim 1, wherein said effector moiety comprises at least one non-metallic radionuclide.

11. The method of claim 1, wherein said effector moiety comprises at least one macrocyclic or non-macrocyclic metal chelating ligand.

12. The method of claim 11, wherein said metal chelating ligand is chelated to a paramagnetic, super-paramagnetic, or radioactive metallic radionuclide.

13. The method of claim 1, wherein said antifolate and folate- or pteroate-conjugate are administered sequentially.

14. The method of claim 1, wherein said antifolate is administered approximately 0 to 12 h prior to administering said folate or pteroate-conjugate.

15. The method of claim 1, wherein said antifolate is administered after administering said folate- or pteroate-conjugate.

16. The method of claim 1, wherein said antifolate is administered together with administering said folate- or pteroate-conjugate.

17. The method of claim 1,
wherein said folate- or pteroate-conjugate is a compound of formula (I)

$$F-S-E \tag{I}$$

wherein
F represents a folate or a pteroate;
S represents a single bond or a spacer, and
E is a pharmaceutically active agent, a non-metallic radionuclide, or a complex C•M, wherein C represents a metal-chelating ligand and M represents a metallic radioisotope chelated by said metal-chelating ligand C.

18. The method of claim 1, wherein said folate- or pteroate-conjugate comprises a folate or pteroate linked directly to said one or more effector moieties.

19. The method of claim 5, wherein said folate or pteroate is folic acid, pteroic acid, folinic acid, or pteropolyglutamic acid, or a salt thereof.

20. The method of claim 1, wherein said antifolate is methotrexate, raltitrexed, pemetrexed, trimetrexate, edatrexate, lometrexol, nolatrexed or aminopterin.

21. The method of claim 1, wherein said antifolate is an inhibitor of dihydrofolate reductase, thymidylate synthase, GARformyltransferase or AICA formyltransferase.

22. The method of claim 1, wherein the antifolate is administered up to 24 hours before the folate- or pteroate-conjugate is administered.

23. The method of claim 1, wherein the antifolate is administered up to 12 hours before the folate- or pteroate-conjugate is administered.

24. The method of claim 1, wherein the antifolate is administered up to 6 hours before the folate- or pteroate-conjugate is administered.

25. The method of claim 1, wherein the antifolate is administered up to 4 hours before the folate- or pteroate-conjugate is administered.

26. The method of claim 1, wherein the antifolate is administered up to 1 hour before the folate- or pteroate-conjugate is administered.

27. The method of claim 1, wherein the antifolate is administered up to 4 hours after the folate- or pteroate-conjugate is administered.

28. The method of claim 1, wherein the antifolate is administered up to 1 hour after the folate- or pteroate-conjugate is administered.

29. The method of claim 1, wherein said diseased cells are ovarian, endometrial, breast, colorectal, kidney, lung, or nasopharyngeal tumour cells.

30. The method of claim 1, wherein said diseased cells are leukaemia cells.

31. The method of claim 1, wherein said diseased cells are activated macrophages in a patient having rheumatoid arthritis.

32. The method of claim 1, wherein the deaza analogs are selected from 1-deaza, 3-deaza, 5-deaza, 8-deaza, and 10-deaza analogs, and dideaza analogs are selected from 1,5 dideaza, 5,10-dideaza, 8,10-dideaza, and 5,8-dideaza analogs.

33. A method for selective targeting of one or more effector moieties to diseased cells in a mammal, said diseased cells expressing or overexpressing a folate receptor, as compared to at least one of normal kidney, lung, choroid plexus or placenta cells expressing a folate receptor, comprising simultaneous or sequential administration of effective amounts of an antifolate, and a folate- or pteroate-conjugate comprising said one or more effector moieties, wherein the folate or pteroate is selected from the group consisting of folic acid, pteroic acid, folinic acid, pteropolyglutamic acid, and folate receptor-binding pteridines selected from the group consisting of tetrahydropterins, dihydrofolates, tetrahydrofolates, and deaza and dideaza analogs thereof, or salt, ester or polyglutamated form thereof;

the amount of antifolate administered is effective to selectively target the folate- or pteroate-conjugate comprising one or more effector moieties to diseased cells as compared to at least one of normal kidney, lung, choroid plexus or placenta cells;

the effector moieties comprise a diagnostic or therapeutic agent;

the amount of folate- or pteroate-conjugate comprising one or more effector moieties is diagnostically or therapeutically effective; and simultaneous or sequential administration of the antifolate and the folate- or pteroate-conjugate is effective to selectively target the effector moiety to diseased cells expressing or overexpressing a folate receptor relative to at least one of normal kidney, lung, choroid plexus or placenta cells expressing a folate receptor, as compared to administration of the conjugate in the absence of an effective amount of the antifolate, wherein sequential administration occurs within 24 hours.

* * * * *